United States Patent
Gholamin et al.

(10) Patent No.: US 11,078,272 B2
(45) Date of Patent: Aug. 3, 2021

(54) TREATMENT OF PEDIATRIC BRAIN TUMORS WITH TARGETING OF CD47 PATHWAY

(71) Applicant: The Board of Trustees of the Leland Stanford Junior University, Stanford, CA (US)

(72) Inventors: Sharareh Gholamin, Pasadena, CA (US); Samuel Cheshier, Palo Alto, CA (US); Siddhartha S. Mitra, Aurora, CO (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 359 days.

(21) Appl. No.: 15/912,447

(22) Filed: Mar. 5, 2018

(65) Prior Publication Data
US 2018/0258170 A1 Sep. 13, 2018

Related U.S. Application Data

(60) Provisional application No. 62/469,378, filed on Mar. 9, 2017.

(51) Int. Cl.
| | | |
|---|---|---|
| C07K 16/28 | (2006.01) | |
| A61P 35/00 | (2006.01) | |
| A61K 9/00 | (2006.01) | |
| A61K 39/00 | (2006.01) | |

(52) U.S. Cl.
CPC ........ *C07K 16/2803* (2013.01); *A61K 9/0004* (2013.01); *A61P 35/00* (2018.01); *A61K 2039/505* (2013.01); *C07K 2317/24* (2013.01); *C07K 2317/52* (2013.01); *C07K 2317/73* (2013.01); *C07K 2317/76* (2013.01)

(58) Field of Classification Search
CPC .................................................. C07K 16/2803
USPC ....................................................... 424/133.1
See application file for complete search history.

(56) References Cited

U.S. PATENT DOCUMENTS

| | | | |
|---|---|---|---|
| 7,514,229 B2 | 4/2009 | Jamieson et al. | |
| 8,361,736 B2 | 1/2013 | Majeti et al. | |
| 8,562,997 B2 | 10/2013 | Jaiswal et al. | |
| 8,709,429 B2 | 4/2014 | Majeti et al. | |
| 8,758,750 B2 | 6/2014 | Weissman et al. | |
| 9,017,675 B2 | 4/2015 | Liu et al. | |
| 9,151,760 B2 | 10/2015 | Weissman et al. | |
| 9,193,955 B2 | 11/2015 | Majeti et al. | |
| 9,382,320 B2 | 7/2016 | Liu et al. | |
| 9,399,682 B2 | 7/2016 | Jaiswal et al. | |
| 2015/0110780 A1 | 4/2015 | Lee et al. | |
| 2015/0183855 A1* | 7/2015 | Diamond | ................ A61P 25/28 424/139.1 |
| 2016/0333093 A1 | 11/2016 | Weiskopf et al. | |

FOREIGN PATENT DOCUMENTS

| | | |
|---|---|---|
| WO | 2012088309 A1 | 6/2012 |
| WO | 2013109752 A1 | 7/2013 |
| WO | 2014149477 A1 | 9/2014 |
| WO | 2014179132 A1 | 11/2014 |
| WO | 2014186761 A2 | 11/2014 |
| WO | 2015105995 A2 | 7/2015 |
| WO | 2015138600 A2 | 9/2015 |
| WO | 2015161267 A2 | 10/2015 |
| WO | 2016022971 A1 | 2/2016 |
| WO | 2016033201 A1 | 3/2016 |
| WO | 2016065329 A1 | 4/2016 |
| WO | 2016179399 A1 | 11/2016 |
| WO | 2016205042 A1 | 12/2016 |
| WO | 2017/035480 A1 | 3/2017 |

OTHER PUBLICATIONS

Gholamin et al (Molecular and Cellular Biology, 2013, 73(8): Abstract 5218).*
Gholamin et al (Neuro-Oncology, 2015, 17(Suppl 5): v118: IMPS-26).*
DeVos et al., "Direct Intraventricular Delivery of Drugs to the Rodent Central Nervous System", Journal of Visualized Experiments, May 12, 2013, pp. 1-10, (75), e50326, Creative Commons Attribution, Mountain View, CA.
Zhang et al., "Anti-CD47 Treatment Stimulates Phagocytosis of Glioblastoma by M1 and M2 Polarized Macrophages and Promotes M1 Polarized Macrophages In Vivo", Plos One, Apr. 19, 2016, pp. 1-21, Plos, San Francisco, CA.
Cabanas et al. (2013) "Treatment of children with high grade glioma with nimotuzumab A 5-year institutional experience" MABS, vol. 5. No. 2, pp. 202-207.
DeVos et al. (2013) "Direct Intraventricular Delivery of Drugs to the Rodent Central Nervous System", Journal of Visualized Experiments, vol. 75. pp. 1-10.
Gholamin et al. (2013) "Abstract 5218 Development of Anti-CD47 therapy for pediatric brain tumors", Cancer Research, AACR Publications, Abstract 5218, XP55746121.
Gholamin et al. (2017) "Disrupting the CD47-SIRPa antiphagocytic axis by a humanized anti-CD47 antibody is an efficacious treatment for malignant pediatric brain tumors" pgs, XP55745619.
Liu et al. (2015) "Pre-Clinical Development of a Humanized Anti-CD47 Antibody with Anti-Cancer Therapeutic Potential". Plos One. vo 1 • 10. No. 9, pp. 1-23.
Lenkov et al. (2016) "Nanoparticle-based translational MR Imaging for immune-therapy trials in glioblastoma", Molecular Imaging & Biology Elsevier Boston, vol. 18. No., pp. 1-1553.
Zhang et al: "Anti-CD47 Treatment Stimulates Phagocytosis of Glioblastoma by M1 and M2 Polarized Macrophages and Promotes M1 Polarized Macrophages In Vivo". Plos One. vol. 11. No. 4. pp. 1-21.

(Continued)

*Primary Examiner* — Sean E Aeder
(74) *Attorney, Agent, or Firm* — Pamela J. Sherwood; Bozicevic, Field & Francis LLP

(57) ABSTRACT

Methods are provided for targeting pediatric brain tumor cells for depletion.

12 Claims, 29 Drawing Sheets
(28 of 29 Drawing Sheet(s) Filed in Color)

(56) References Cited

OTHER PUBLICATIONS

Zhu et al. (2017) "Surgical debulking promotes recruitment of macrophages and triggers glioblastoma phagocytosis in combination with CD47 blocking immunotherapyn" Oncotarget. Impact Journals LLC. United Statesvo 1. 8. No. 7, pp. 12145-12157.

* cited by examiner

FIG. 1A
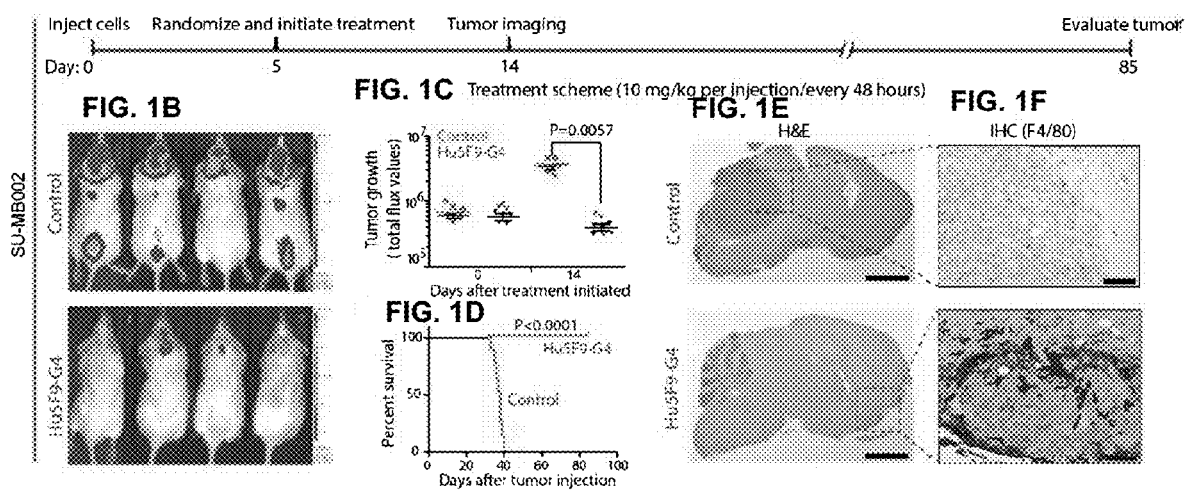
FIG. 1B FIG. 1C FIG. 1E FIG. 1F
FIG. 1D
FIG. 1G FIG. 1I FIG. 1J FIG. 1K
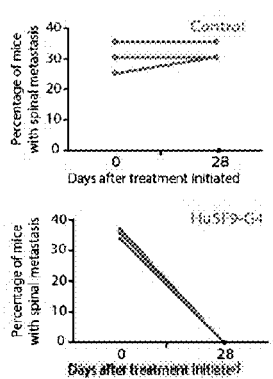
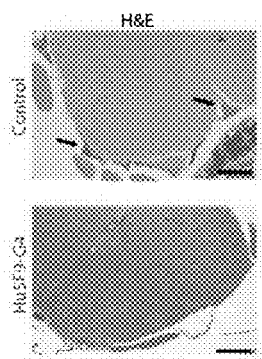
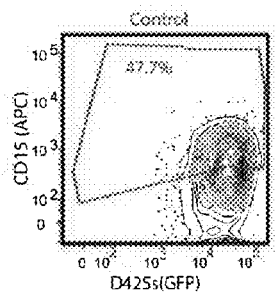
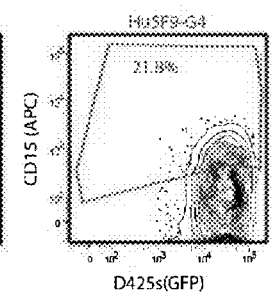
FIG. 1H FIG. 2A
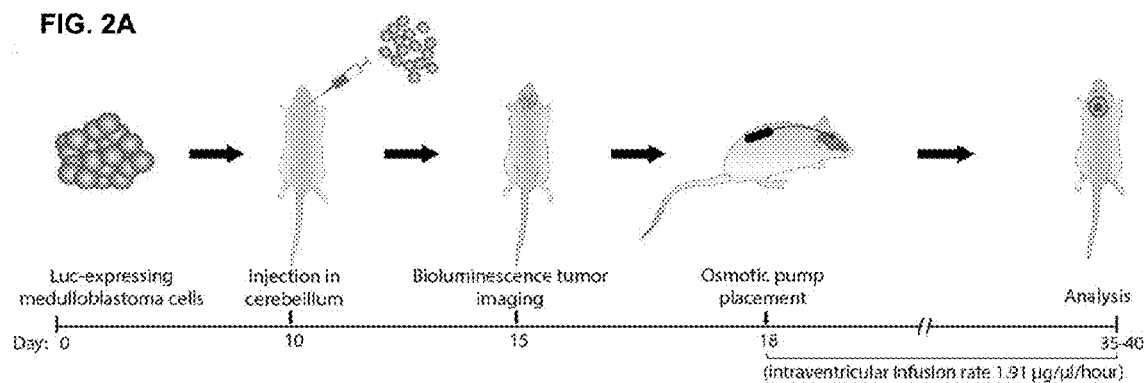
FIG. 2B
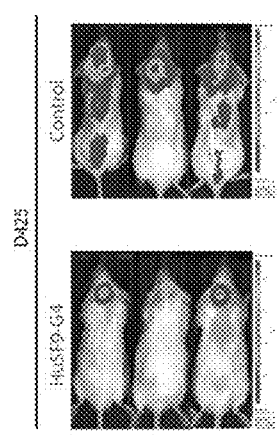
FIG. 2C
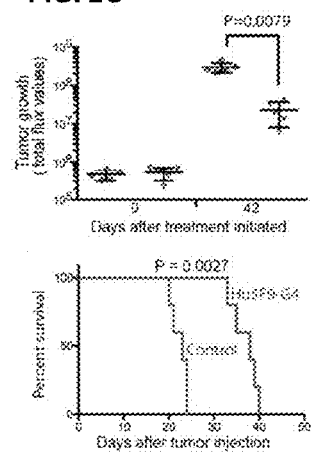
FIG. 2E   FIG. 2F
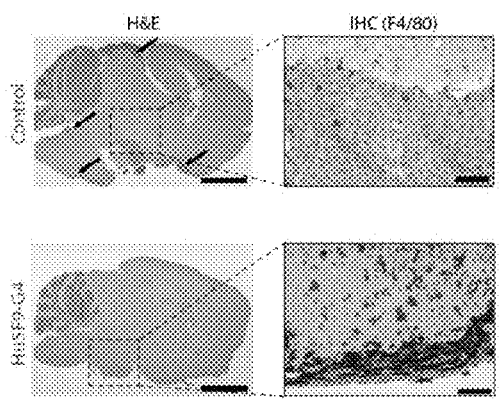
FIG. 2D
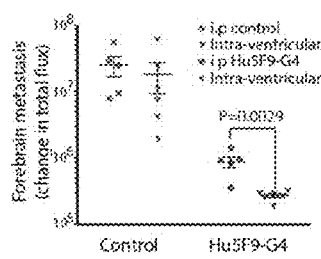
FIG. 2G
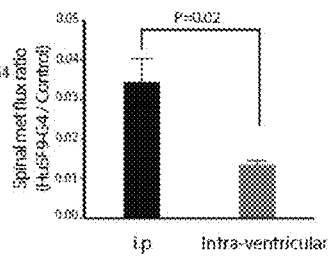
FIG. 2H
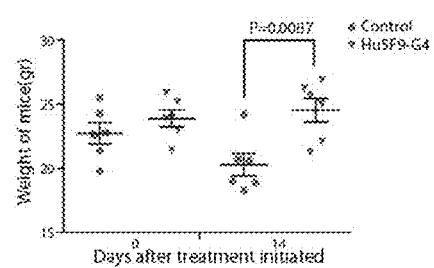
FIG. 2I

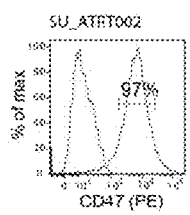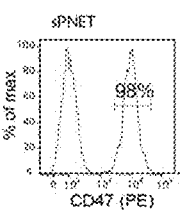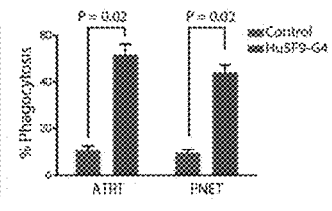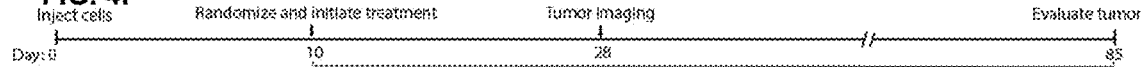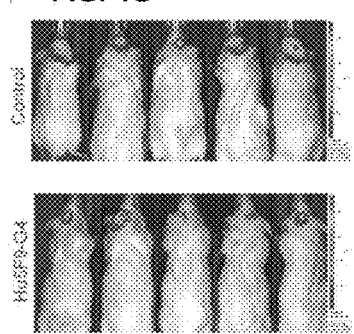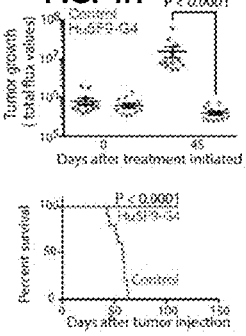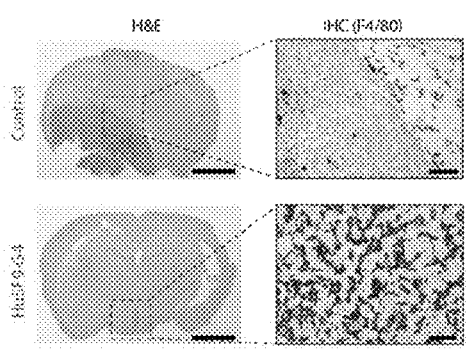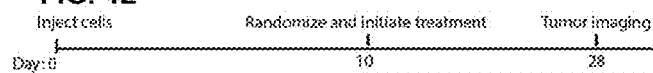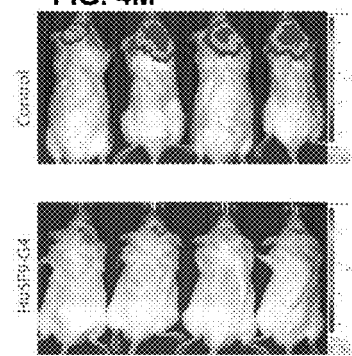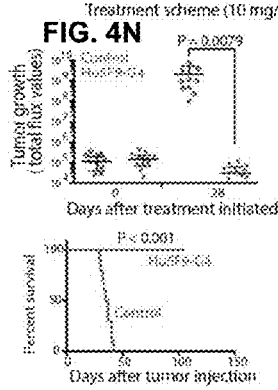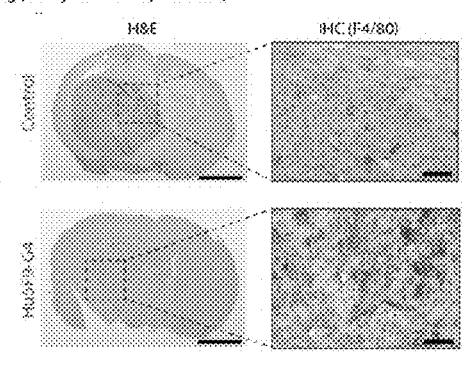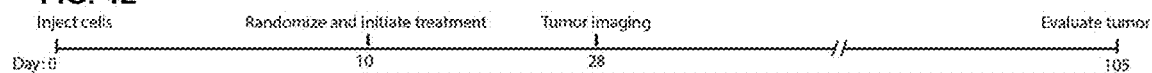

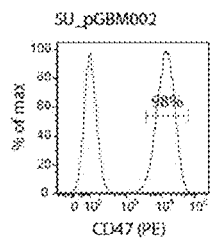
FIG. 5A
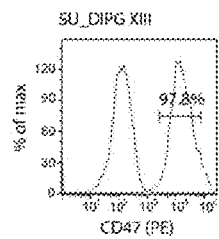
FIG. 5B
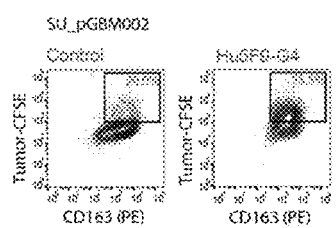
FIG. 5E
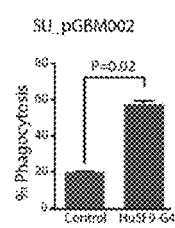
FIG. 5F
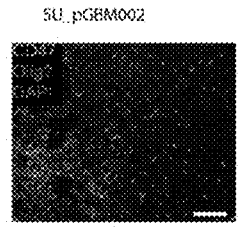
FIG. 5C
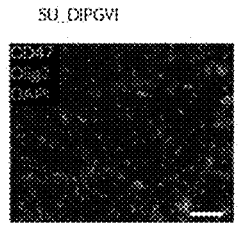
FIG. 5D
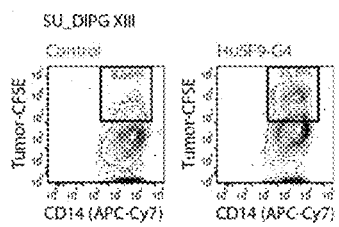
FIG. 5G
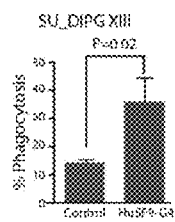
FIG. 5H
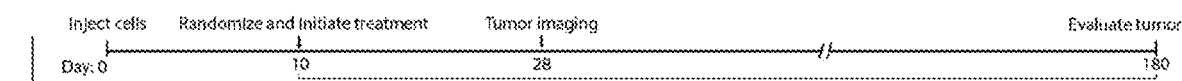
FIG. 5I
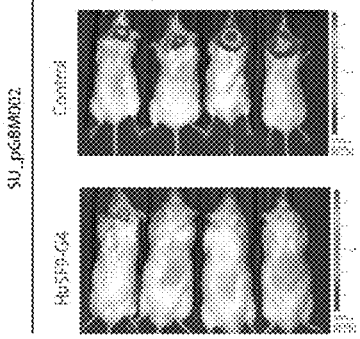
FIG. 5J
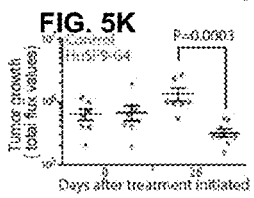
FIG. 5K
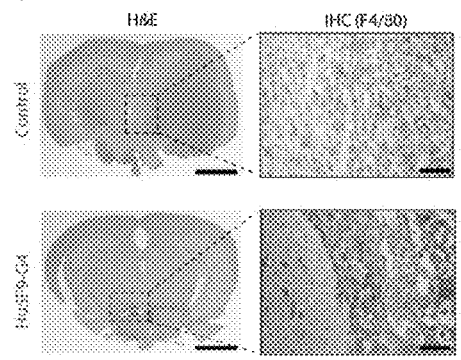
FIG. 5L / FIG. 5M / FIG. 5N
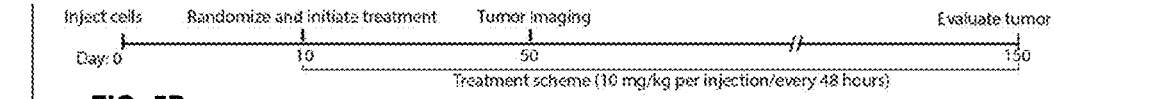
FIG. 5O
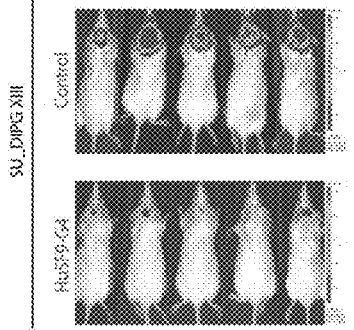
FIG. 5P
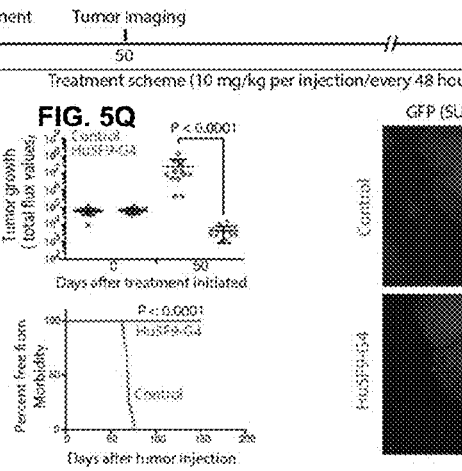
FIG. 5Q
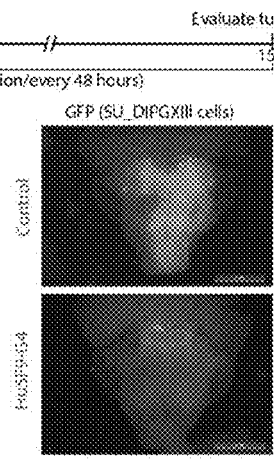
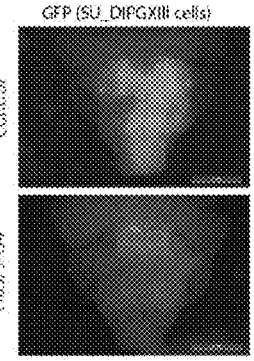
FIG. 5R    FIG. 5S

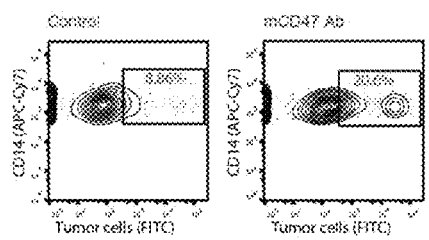
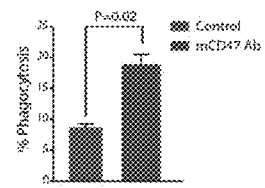
FIG. 6A  FIG. 6B
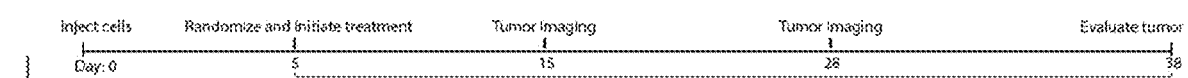
FIG. 6C
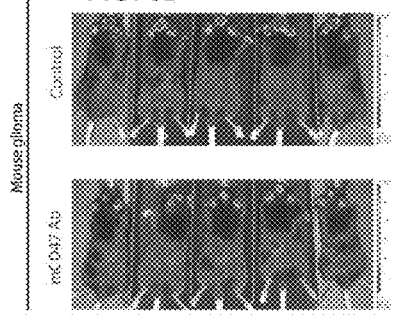
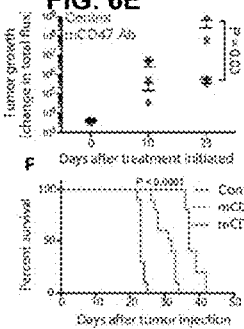
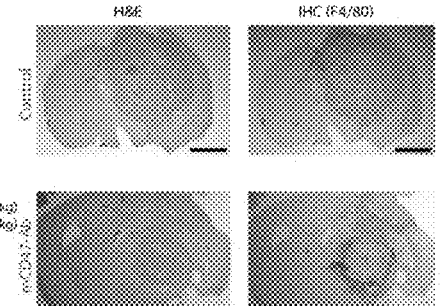
FIG. 6D  FIG. 6E  FIG. 6G  FIG. 6H
FIG. 6F
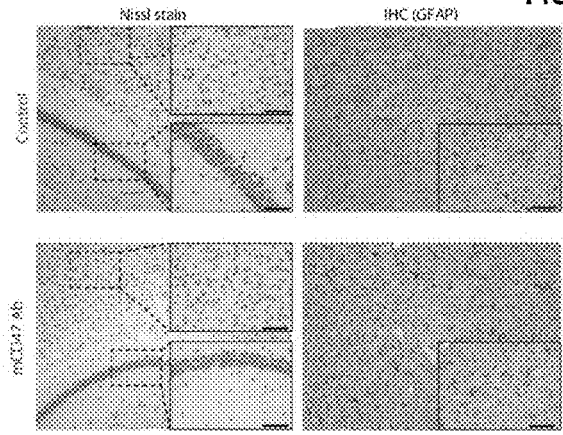
FIG. 6I  FIG. 6J

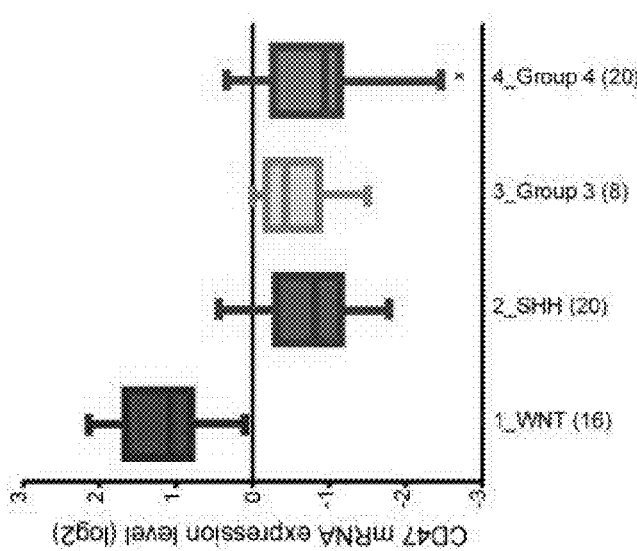
FIG. 7D Heidelberg medulloblastoma
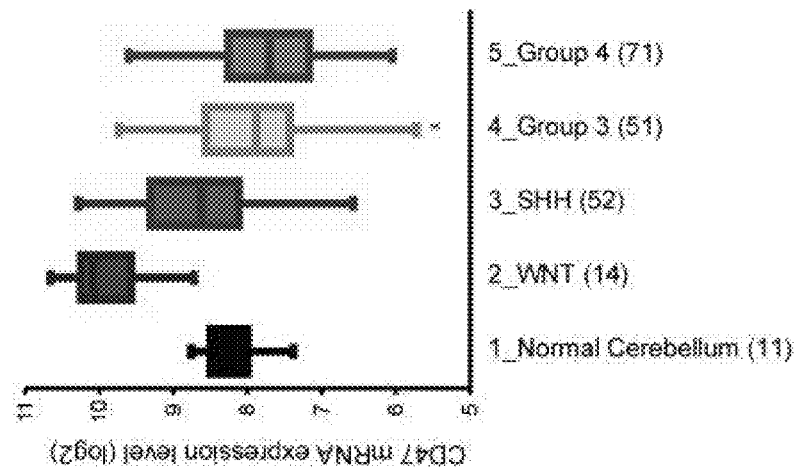
FIG. 7C Boston medulloblastoma
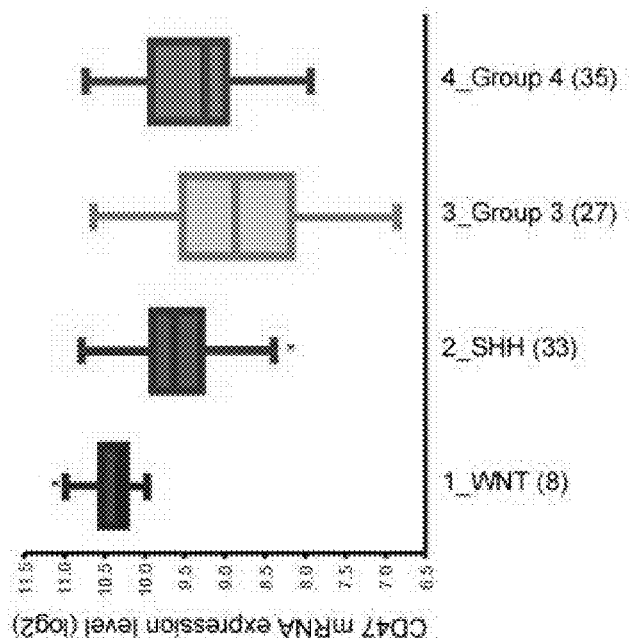
FIG. 7B Toronto medulloblastoma

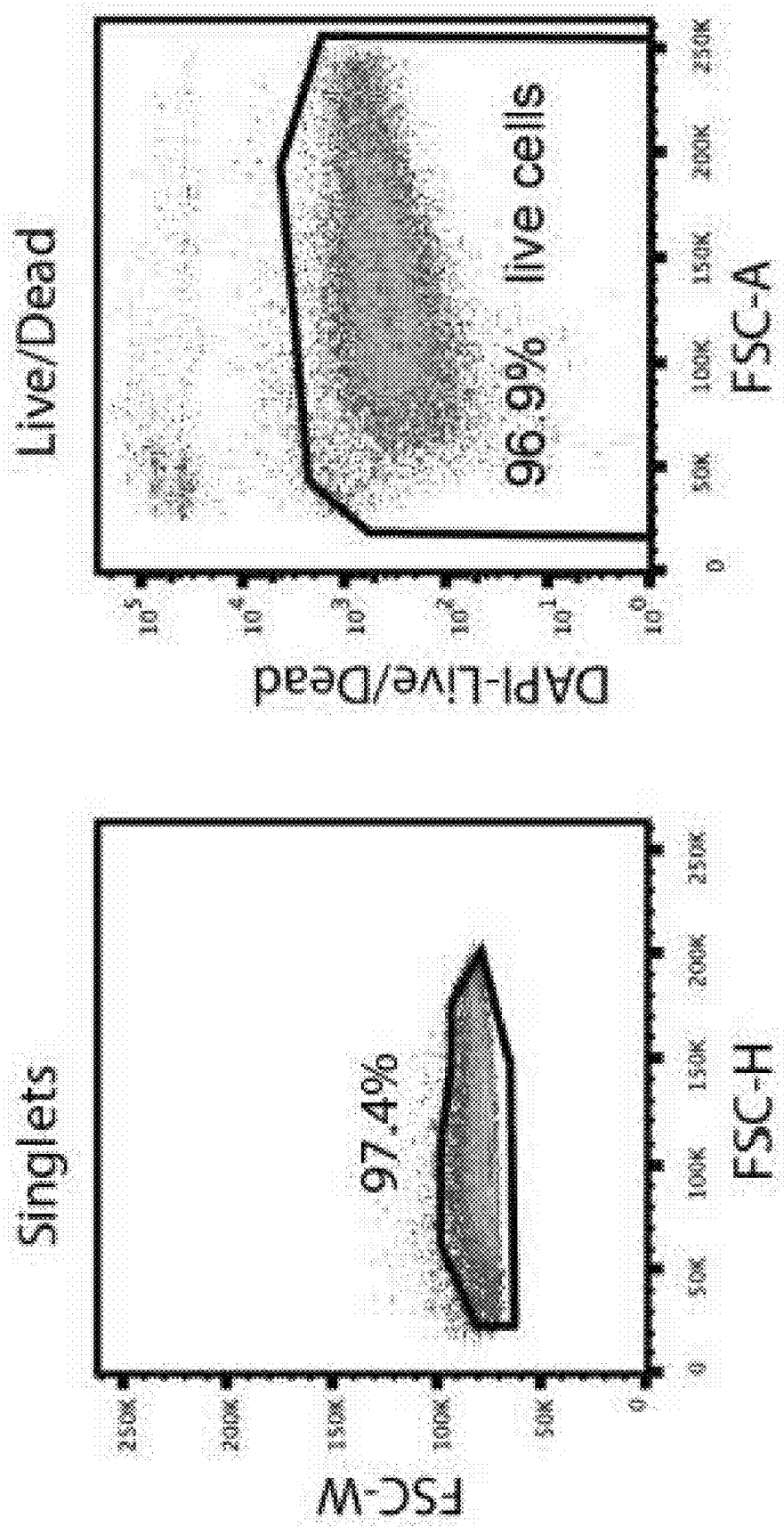
FIG. 9A(ii)

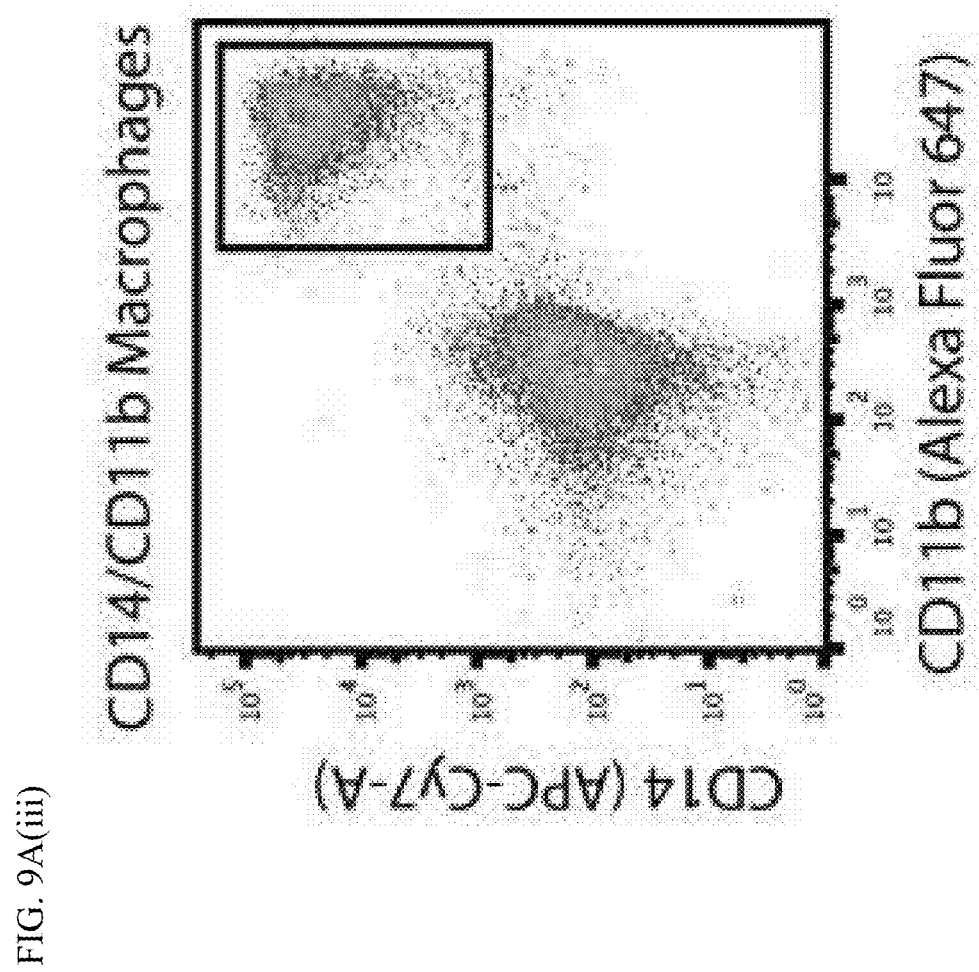
FIG. 9A(iii)

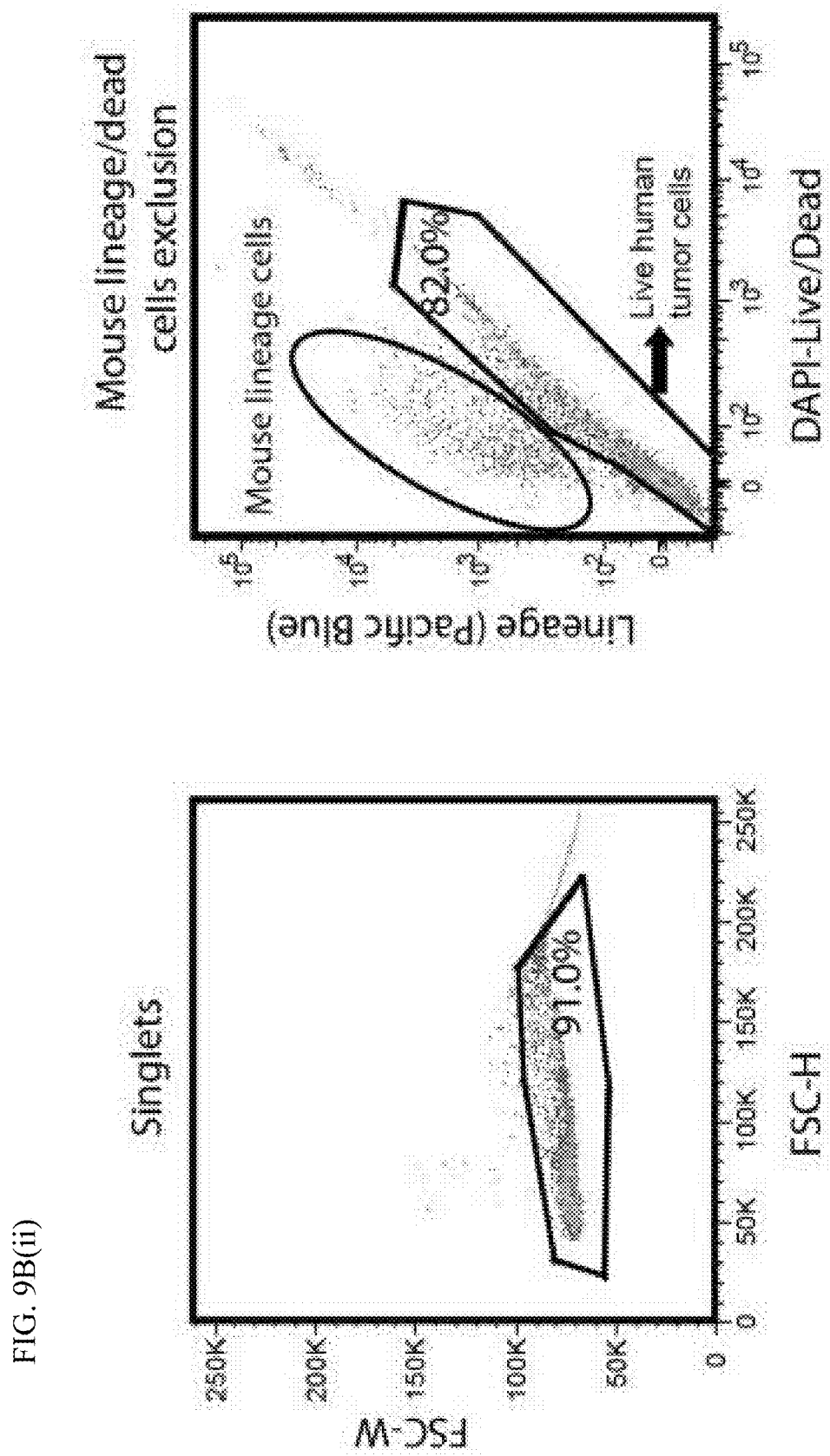
FIG. 9B(ii)

FIG. 11B
SU_MB002
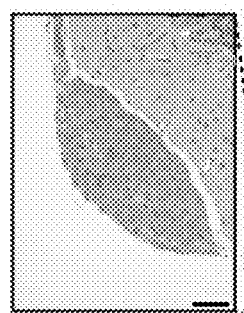
FIG. 11A
FIG. 11D
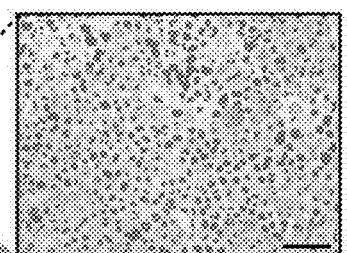
FIG. 11C
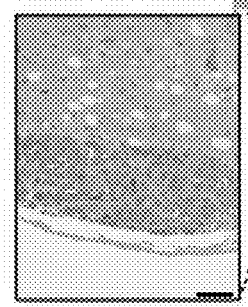
FIG. 11E
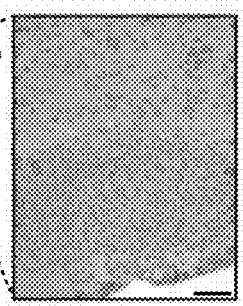
D425s
FIG. 11F
FIG. 11G
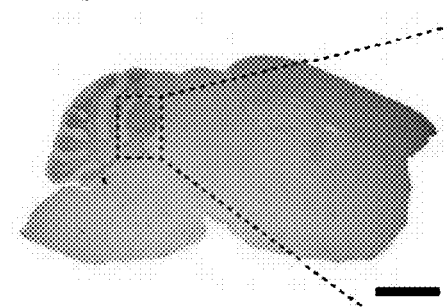
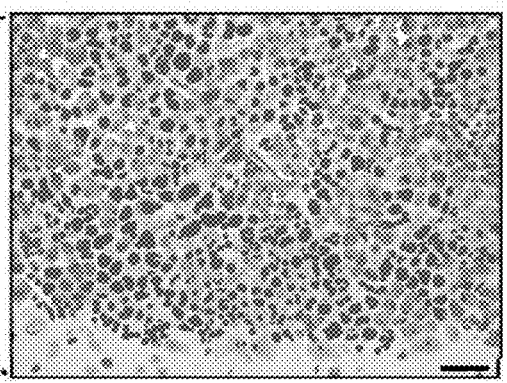

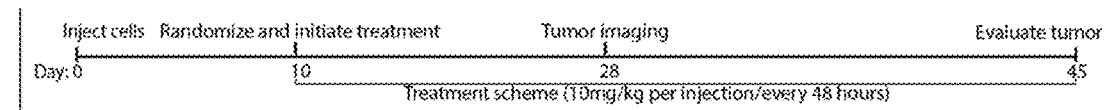
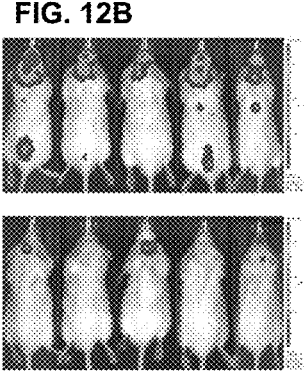
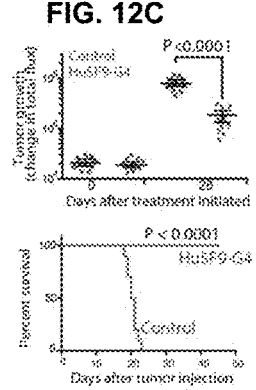
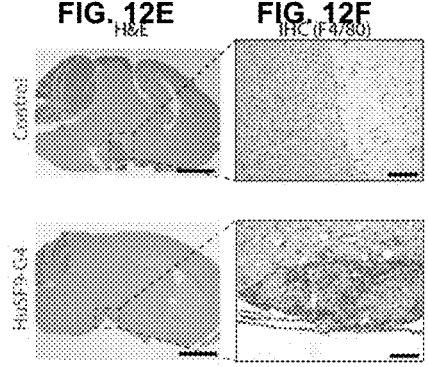
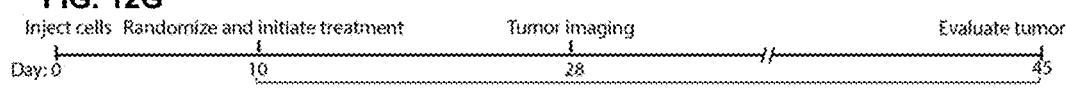
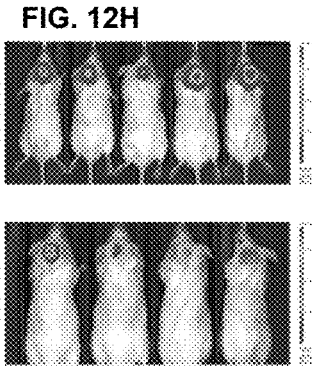
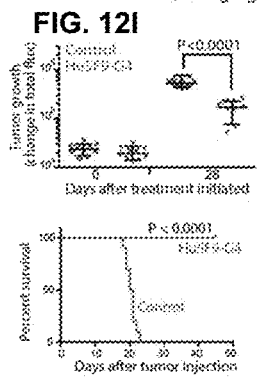
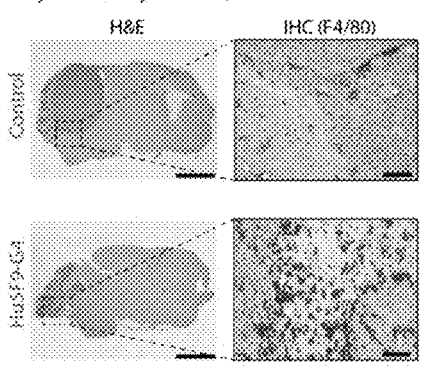
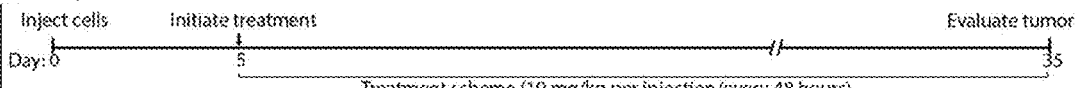
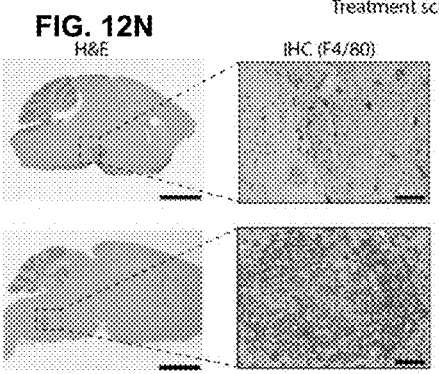
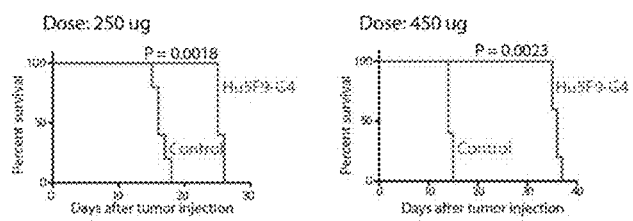

FIG. 14A
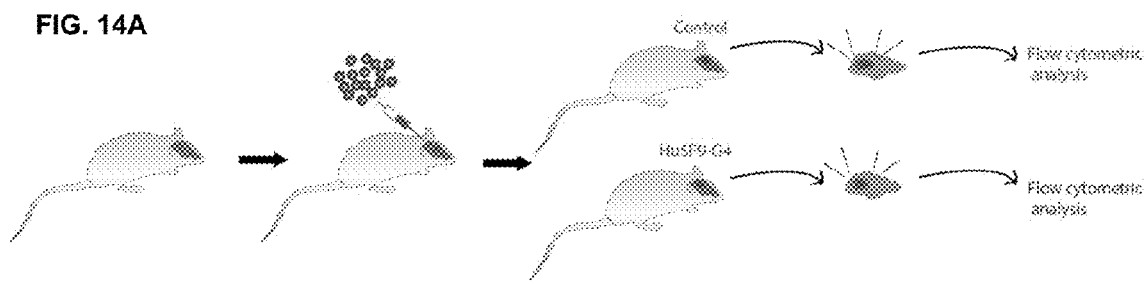
FIG. 14B
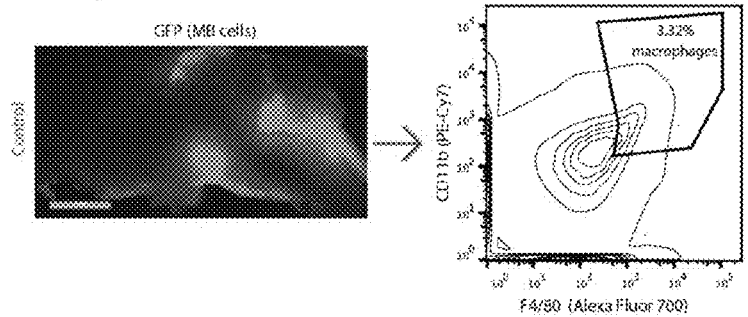
FIG. 14C
FIG. 14D
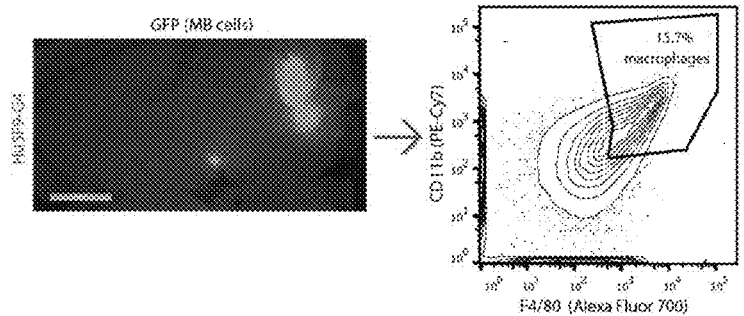
FIG. 14E
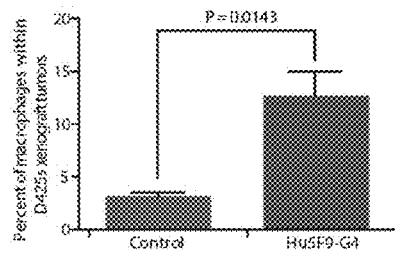
FIG. 14F

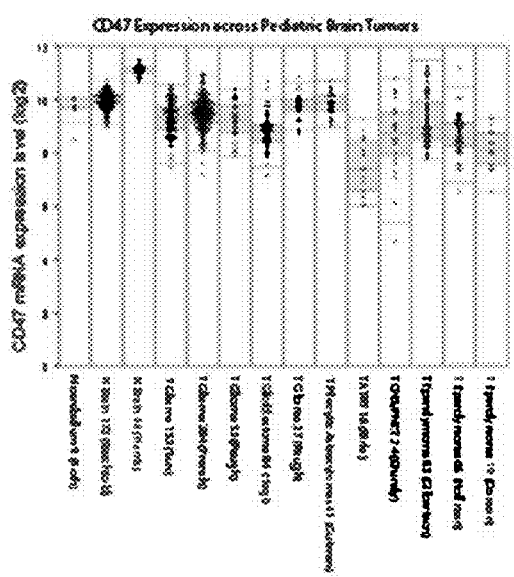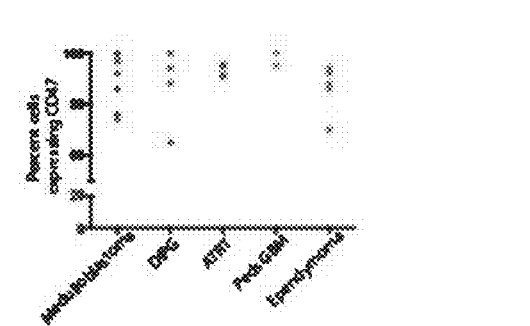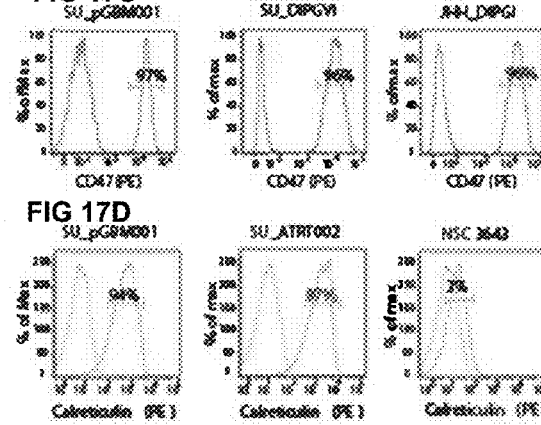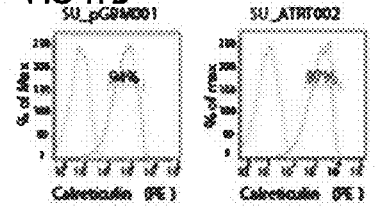

FIG. 20A
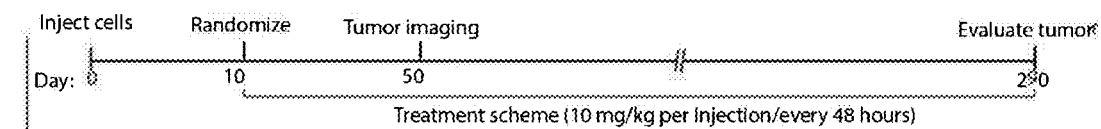
FIG. 20B
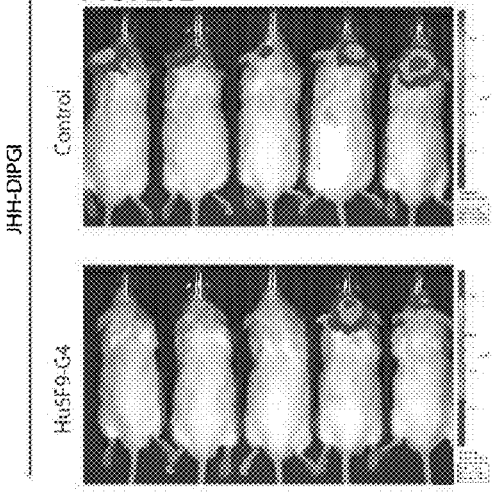
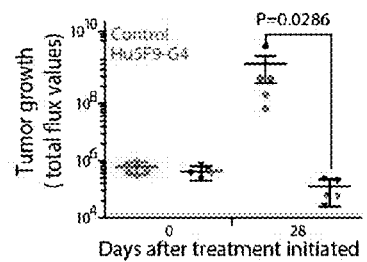
FIG. 20C
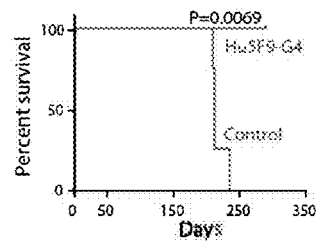
FIG. 20D

FIG. 21A
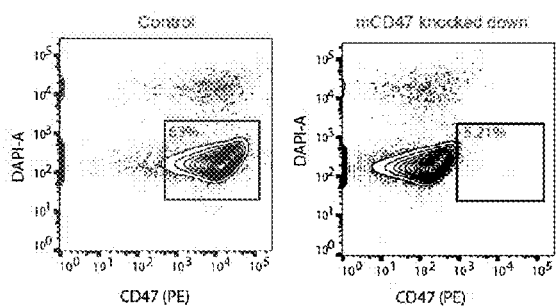
FIG. 21B
FIG. 21C
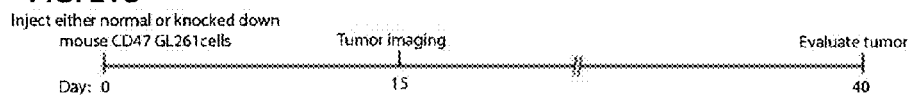
FIG. 21D
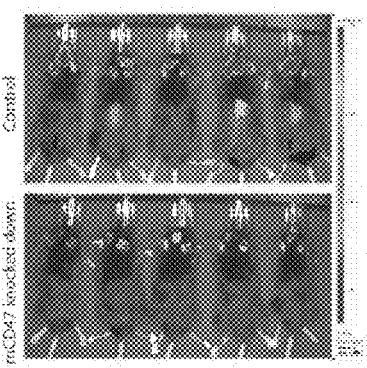
FIG. 21E
FIG. 21G
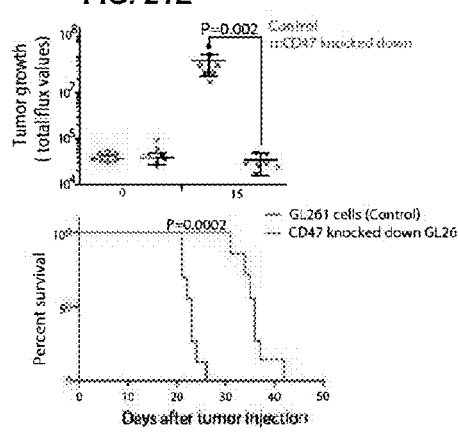
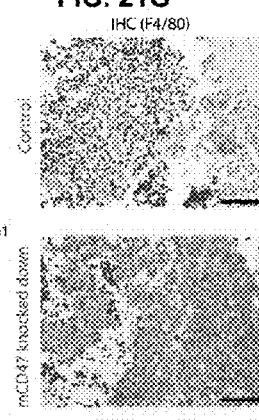
FIG. 21F

TREATMENT OF PEDIATRIC BRAIN TUMORS WITH TARGETING OF CD47 PATHWAY

CROSS REFERENCE

This application claims benefit of U.S. Provisional Patent Application No. 62/469,378, filed Mar. 9, 2017 which application is incorporated herein by reference in its entirety.

The immune system's natural capacity to detect and destroy abnormal cells may prevent the development of many cancers. However, cancer cells are sometimes able to avoid detection and destruction by the immune system. Cancer cells can reduce the expression of tumor antigens on their surface, making it harder for the immune system to detect them; express proteins on their surface that induce immune cell inactivation; and/or induce cells in the microenvironment to release substances that suppress immune responses and promote tumor cell proliferation and survival.

Cancer immunotherapies have been developed to enhance immune responses against tumors, by stimulating specific components of the immune system; or by counteracting signals produced by cancer cells that suppress immune responses. Forms of immunotherapy include blocking immune checkpoint proteins, providing agonists of immune modulators to enhance responsiveness; and the use of antibodies and other agents targeted to tumor specific antigens.

Other forms of immunotherapy exploit the innate immune system. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte, or the loss of CD47 expression in knockout mice, can cause removal of live cells and non-aged erythrocytes. Alternatively, blocking SIRPα recognition also allows engulfment of targets that are not normally phagocytosed. Anti-CD47 antibody treatment has also been shown to not only enable macrophage phagocytosis of cancer, but can also initiate an anti-tumor cytotoxic T cell immune response.

Malignant pediatric brain tumors are etiologically distinct from adult brain tumors and responsible for the highest morbidity and mortality among all pediatric malignancies. Childhood malignant gliomas rapidly infiltrate adjacent brain tissue and are difficult to treat, with extremely poor prognosis. In contrast, pediatric embryonal tumors, namely medulloblastoma (MB), atypical teratoid rhabdoid tumor (ATRT), and primitive neuroectodermal tumor (PNET) have relatively better survival after treatment; however, effective disease control is usually associated with severe physical and intellectual disabilities as well as later development of secondary malignancies. Moreover, when embryonal tumors occur in patients less than 3 years old (as they often do), cranial-spinal irradiation therapy cannot be administered, making these tumors quite deadly in this age group, because they are not responsive to chemotherapies.

Blocking the CD47-SIRPα interaction with a mouse anti-human CD47 mAb has the potential to effectively treat several solid tumors, including adult glioblastoma multiforme (GBM), whereas normal (non-neoplastic) cells are not affected by CD47-blocking antibodies.

The development of effective cancer therapy is of great clinical interest, and is addressed herein.

Related publications include U.S. Pat. Nos. 8,562,997; 9,399,682; 9,017,675; 9,382,320; 9,151,760; 8,758,750; 8,361,736; 8,709,429; 9,193,955; and 7,514,229 and International Patent Applications US2016/049016; US2016/030997; US2016/036520; US2015/046976; US2015/044304; US2015/057233; US2015/026491; US2015/019954; US2015/010650; US2014/035167; US2014/018743; US2014/038485; US2013/021937; and US2011/066580, each herein specifically incorporated by reference.

SUMMARY OF THE INVENTION

Methods are provided for improved treatment of pediatric brain tumors, including reduction of metastasis, e.g. reduction of disseminated leptomeningeal or spinal disease. In the methods of the invention, pediatric brain tumor cells are contacted with an agent that blocks signaling between CD47 and SIRPα, which may be referred to herein as an anti-CD47 agent. The methods of the invention can provide for increased overall survival of the individual being treated, and a significant decrease in tumor volume.

In some embodiments, the pediatric brain tumor is a malignant glioma, for example a high grade glioblastoma, or a diffuse intrinsic pontine gliomas. In some embodiments the pediatric brain tumor is a pediatric embryonal tumor. In some such embodiments, the pediatric brain tumor is medulloblastoma; including without limitation a group 3 medulloblastoma (which are often associated with myc amplification and with classic or large cell/anaplastic morphology). In other such embodiments, the pediatric brain tumor is an atypical teratoid rhabdoid tumor (ATRT). In other such embodiments the pediatric brain tumor is a primitive neuroectodermal tumor (PNET). In some embodiments the pediatric brain tumor is a spinal cord tumor, including without limitation ependydomas.

In some embodiments, administration of an anti-CD47 agent is combined with surgical resection. In other embodiments, surgical resection is not an option for the tumor, e.g. with brain stem or cerebellar tumors. In some embodiments, administration of an anti-CD47 agent is combined with chemotherapy, with tumor specific antibodies, with radiation therapy, with an immuno-oncology agent such as a checkpoint inhibitor, agonist of an immune response protein, and the like.

In some embodiments the anti-CD47 agent is delivered as continuous intraventricular CNS administration. In some embodiments, intraventricular administration is combined with systemic administration. In some embodiments intraventricular administration utilizes an implantable device to deliver the anti-CD47 agent. In some embodiments the implantable device is an osmotic pump. In some embodiments, the device delivers the anti-CD47 agent at a dose of from about 1 mg/kg, from about 5 mg/kg, from about 10 mg/kg, up to about 50 mg/kg, up to about 25 mg/kg, up to about 15 mg/kg, delivered over a period of about 1 day, about 2 days, about 3 days, about 4 days, about 5 days, about 6 days, about 1 week, about 2 weeks; or more. The device may be implanted intraventricularly, for example, with a conventional stereotaxic apparatus.

When combinations of agents are provided, the agents in the combination are administered concomitantly, i.e. each agent is administered within about 45 days, 30 days, 15 days, 7 days, 3 days, 2 days, 1 day or substantially simultaneously with respect to the other agent(s) in the combination. The agents can be considered to be combined if administration scheduling is such that the serum level of both agents is at a therapeutic level. Administration may be repeated as necessary for depletion of the cancer cell population.

In some embodiments a primer agent is administered prior to administering a therapeutically effective dose of an anti-CD47 agent to the individual. Suitable primer agents include an erythropoiesis-stimulating agent (ESA), and/or a priming dose of an anti-CD47 agent. Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered. In some embodiments a therapeutically effective dose of an anti-CD47 agent is administered as two or more doses of escalating concentration, in others the doses are equivalent.

In some embodiments, administration of a combination of agents of the invention is combined with an effective dose of an agent that increases patient hematocrit, for example erythropoietin stimulating agents (ESA). Such agents are known and used in the art, including, for example, Aranesp® (darbepoetin alfa), Epogen®NF/Procrit®NF (epoetin alfa), Omontys® (peginesatide), Procrit®, etc.

An anti-CD47 agent for use in the methods of the invention interferes with binding between CD47 present on the cancer cell and SIRPα present on a phagocytic cell. Such methods, in the presence of the anti-EGFR antibody, can increase phagocytosis of the cancer cell. Suitable anti-CD47 agents include soluble SIRPα polypeptides; soluble CD47; anti-CD47 antibodies, anti-SIRPα antibodies, and the like, where the term antibodies encompasses antibody fragments and variants thereof, as known in the art. In some embodiments the anti-CD47 agent is an anti-CD47 antibody. In some embodiments the anti-CD47 antibody is a non-hemolytic antibody. In some embodiments the antibody comprises a human IgG4 Fc region.

The contacting of a cancer cells may be performed in vivo, e.g. for therapeutic or screening purposes, and in vitro, e.g. for screening assays and the like. In some embodiments, an animal model is provided for testing the toxicity of a therapeutic regimen for treatment of brain cancer. Adverse effects of a regimen on proliferating neural progenitor cells is a concern, particularly for pediatric patients. An in vivo sequential co-transplant xenograft cytotoxicity model is provided, where human fetal-derived neural progenitor cells engineered to express a detectable marker, e.g. a fluorescent or luminescent protein, are injected into the ventricle of an animal brain, e.g. a mouse, rat, etc. After a period of time sufficient for engraftment of the neural progenitor cells, the animal is injected with unlabeled brain tumor cells. Human neural cell viability and proliferation were measured through subsequent bioluminescent imaging assays to determine the effect of treatment on normal cells. In some embodiments a therapeutic regimen is tested for safety on proliferating neural progenitor cells prior to patient administration.

BRIEF DESCRIPTION OF THE FIGURES

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1K. Hu5F9-G4 inhibits primary and metastatic medulloblastoma in vivo. (FIG. 1A) Treatment scheme for evaluation of in vivo efficacy of Hu5F9-G4. (FIG. 1B, FIG. 1C) Representative image (FIG. 1B) and quantitation of BLI (FIG. 1C) of patient-derived cMYC amplified MB (shown: SU-MB002) xenograft from Hu5F9-G4 treated and control mice. Hu5F9-G4 treated mice showed significant decrease in tumor burden compared with control mice (P=-0.0057). (FIG. 1D) Hu5F9-G4 significantly increased survival of mice with cMYC amplified tumors (n=8 per group, P<0.0001, log-rank analysis). (FIG. 1E) H&E staining of sagittal sections from mice treated with Hu5F9-G4 showed reduction of tumor size at the primary cerebellar site of transplantation as well as elimination of leptomeningeal disease (scale bars, 2 mm). (FIG. 1F) Immunostaining with anti-F4/80 antibody showed increased macrophage accumulation at tumor sites after treatment with Hu5F9-G4 (scale bars, 50 µm). (FIG. 1G, FIG. 1H) Percentage of mice with spinal metastasis before and after treatment with either control (FIG. 1G) or Hu5F9-G4 (FIG. 1H). Each line represents an independent experiment (n=3) with 8-10 mice in each arm per experiment. (FIG. 1I) H&E staining of spinal cord sections from mice treated with control or Hu5F9-G4 (scale bars, 200 µm). Metastatic tumors are shown with arrows. (FIG. 1J, FIG. 1K) Representative flow cytometric plots of dissociated NSG mouse brains transplanted with human MB cells. Human MB-initiating cells were identified as $CD15^+GFP^+$ $msLIN^-$ cells. Treatment with Hu5F9-G4 (FIG. 1J) reduced the percentage of human MB-initiating cells compared to the control counterpart (FIG. 1K).

FIG. 2A-2I. Intraventricular infusion of Hu5F9-G4 accelerates anti-metastatic activity. (FIG. 2A) Schematic representation of intraventricular infusion experiment. Osmotic pumps loaded with Hu5F9-G4 were implanted into mice for direct ventricular infusion into the lateral ventricle after tumor formation was confirmed by BLI imaging. (FIG. 2B, FIG. 2C) Representative BLI images (FIG. 2B) and quantitation (FIG. 2C) after 30 days of intraventricular infusion. (FIG. 2D) Kaplan-Meier analysis of mice infused with Hu5F9-G4 and control (n=10 per group, P=0.0027, log-rank analysis). (FIG. 2E) H&E staining reveals presence of primary cerebellar tumor in both the control and Hu5F9-G4-treated mice, with lack of ventricular and leptomeningeal metastasis in the forebrain (scale bars, 2 mm) of Hu5F9-G4 treated mice. (FIG. 2F) Infiltration of macrophages in Hu5F9-G4 treated mice as visualized by F4/80 macrophage staining (scale bars, 50 µm). (FIG. 2G) Comparative analysis of tumor burden in mice treated by intraperitoneal injection (circle) or intraventricular infusion (triangle), showing accelerated antitumor effect on forebrain leptomeningeal tumor spread with intraventricular infusion. (FIG. 2H) Ratio of spinal metastasis flux in Hu5F9-G4-treated to control mice after 14 d of treatment. (FIG. 2I) The weight of mice with intraventricular Hu5F9-G4 or control 14 d after initiation of treatment.

(FIG. 3A) In vitro experimental design to assay Hu5F9-G4 selectivity. Color-coded neural progenitor cells (NPCs, red) and tumor cells (green) were co-incubated with macrophages in the presence of Hu5F9-G4 and assayed for phagocytosis. (FIG. 3B, FIG. 3C) Flow cytometry (FIG. 3B) and histogram (FIG. 3C) plots show more phagocytosis of tumor cells by macrophages in the presence of Hu5F9-G4, whereas the percentage of phagocytized NPCs was low with both control and Hu5F9-G4 treatments. The color-coded tumor cells and NPCs were analyzed in the FITC and PE channels, respectively. (FIG. 3D) Schematic representation of experimental design to test for in vivo cytotoxic effect on human NPCs in tumor-bearing mice. Unlabeled human medulloblastoma cells (SU_MB002) were injected into mice with previously engrafted luciferase-expressing human NPCs and treated with Hu5F9-G4 or control. Note: in this experiment, BLI was observed from the human NPCs and not from the tumor cells. (E,F) BLI images (FIG. 3E) and measures (FIG. 3F) show no statistically significant change in growth of NPCs in mice treated with control or Hu5F9-G4 (control=8, Hu5F9-G4=7, P=0.11). (FIG. 3G) Improved survival was seen in the mice treated with Hu5F9-G4 compared to the control group (P<0.0001).

FIGS. 4A-4Q. Hu5F9-G4 targets human ATRT and PNET in vitro and in vivo. (FIG. 4A, FIG. 4B) Flow cytometric plots of cell surface expression of CD47 on primary ATRT (FIG. 4A) and PNET (FIG. 4B) cell lines. More than 95% of cells express CD47 on their surface. (FIG. 4C, FIG. 4D) Expression of CD47 on fresh frozen primary ATRT (FIG. 4C) and PNET (FIG. 4D) surgical specimens (scale bars, 50 µm). (FIG. 4E) ATRT or PNET cells were incubated with human macrophages in the presence of Hu5F9-G4 or human IgG, and phagocytosis was observed by fluorescence microscopy. Hu5F9-G4 significantly enhanced phagocytosis of ATRT cells (P=0.02) and PNET cells (P=0.02). (FIG. 4F) A treatment scheme for mice bearing SU_ATRT002. (FIG. 4G, FIG. 4H) BLI images (FIG. 4G) and measurements (FIG. 4H) of SU_ATRT002 xenografts treated with either HuF59-G4 or control (P<0.0001). (FIG. 4I) Significant survival extension was observed in mice upon Hu5F9-G4 treatment (n=10 per group, P<0.0001, log-rank analysis). (FIG. 4J) H&E staining of the control and HuF59-G4-treated SU_ATRT002 xenografts (scale bars, 2 mm). (FIG. 4K) F4/80 staining of macrophages showed increased infiltration of macrophages in tumors treated with Hu5F9-G4 compared to controls (scale bars, 50 µm). (FIG. 4L) A treatment scheme of the mice xenografted with sPNET. (M,N) BLI images (FIG. 4M) and measures (FIG. 4N) of mice bearing PNET 28 d after treatment with either HuF59-G4 or control (P=−0.0079). (FIG. 4O) Significant increase in survival of PNET xenografts treated with HuF59-G4 was seen compared to the control group (sPNET: n=10 per group, P<0.0001, log-rank analysis). (FIG. 4P) H&E staining of the control and HuF59-G4-treated mouse xenografts showed the presence of very small residual tumors in the treated group compared with the controls (scale bars, 2 mm). (FIG. 4Q) F4/80 staining of macrophages showed increased infiltration of macrophages in tumors treated with Hu5F9-G4 compared to controls (scale bars, 50 µm).

FIG. 5A-5S. Hu5F9-G4 targets pediatric GBM and DIPG in vitro and in vivo. (A,B) Representative flow cytometric plots of surface expression of CD47 on pGBM (FIG. 5A) and DIPG (FIG. 5B). (FIG. 5C, FIG. 5D) Immunofluorescence analysis of CD47 (green) and Olig2 (red) in pGBM (FIG. 5C) and DIPG (FIG. 5D) fresh frozen patient samples (scale bars, 50 µm). DAPI nuclear stain is blue. (FIG. 5E, FIG. 5F) The phagocytosis assay of SU_pGBM002 by macrophages in the presence and absence of Hu5F9-G4, shown by flow cytometry plots (FIG. 5E) and histograms (FIG. 5F). (FIG. 5G, FIG. 5H) The phagocytosis of SU_DIPGXIII cells by macrophages in the presence or absence of Hu5F9-G4, shown by flow cytometry plots (FIG. 5G) and histograms (FIG. 5H). (FIG. 5I) A treatment scheme of SU-pGBM002 bearing mice. Luciferase-expressing SU_pGBM002 cells were injected into the left hemisphere of NSG mice. The treatment commenced after tumor was detected by BLI imaging. (FIG. 5J, FIG. 5K) BLI images (FIG. 5J) and measures (FIG. 5K) were analyzed after 28 d of treatment with either control or Hu5F9-G4. (FIG. 5L) A significant increase in survival was observed after Hu5F9-G4 administration in treated groups versus the controls (control=7, Hu5F9-G4=8, P<0.0001, log-rank analysis). (FIG. 5M) H&E staining of SU_pGBM002 xenografted mouse revealed the spread of tumor in the control versus the treated group (scale bars, 2 mm). (FIG. 5N) F4/80 staining of xenografted mouse brains showed increased infiltration of macrophages in Hu5F9-G4-treated tumor compared to the control (scale bars, 50 µm). (FIG. 5O) A treatment scheme of SU_DIPGXIII xenografts. SU_DIPGXIII cells were injected into the pons of NSG mice. (FIG. 5P, FIG. 5Q) BLI images (FIG. 5P) and quantities (FIG. 5Q) revealed a significant decrease of tumor size in treated mice with Hu5F9-G4 compared to the control (P<0.0001). (FIG. 5R) A significant increase in survival was observed after Hu5F9-G4 administration in treated groups versus the control counterparts (SU_DIPGXIII, control=12, Hu5F9-G4=13, P<0.0001, log-rank analysis). (FIG. 5S) Efficacy of Hu5F9-G4 treatment against DIPG is represented by stereo fluorescence whole mount microscopy in mice with GFP-expressing SU_DIPGXIII xenografted into the pons (scale bars, 5 mm).

FIG. 6A-6J. Anti-mouse CD47 mAb inhibits tumor growth in immunocompetent host. (FIG. 6A, FIG. 6B) Flow cytometric plots (FIG. 6A) and the histogram (FIG. 6B) show significantly higher phagocytosis of GL261 cells by macrophages in the presence of mCD47 mAb compared with the control (P=0.02). (FIG. 6C) Schematic of in vivo experimental time course. (FIG. 6D, FIG. 6E) BLI imaging (FIG. 6D) and measures (FIG. 6E) revealed smaller tumors and a significantly slower tumor growth in mice treated with mCD47 mAb compared with the control group (P=0.03). (FIG. 6F) Significantly extended and dose-dependent survival was seen in GL261 tumor-bearing mice treated with mCD47 mAb versus the control group (n=5 per group, P<0.0001, log-rank analysis). (FIG. 6G, FIG. 6H) H&E showed lower tumor burden (FIG. 6G), and immunostaining for mouse macrophages (F4/80) (FIG. 6H) showed increased recruitment of macrophages in the treated brains compared with controls (scale bars, 2 mm). (FIG. 6I, FIG. 6J) Histoarchitecture analysis by staining of neurons using cresyl violet stain (FIG. 6I) and astrocytes using anti-GFAP antibody (FIG. 6J) revealed no damage to neurons and astrocytes or presence of gliosis after treatment with mCD47 mAb in the treated brains compared with controls (scale bars, 50 µm).

FIG. 7A-7G. Expression analysis of CD47 and cell surface calreticulin in medulloblastoma. (FIG. 7A) Expression analysis of CD47 from the R2 dataset. Y-axis label is Log 2 expression and expression values are depicted as Box-Dot-Plot. Box plot component: In this plot type, the middle 50 percent of the data is represented by a box. The median forms a horizontal line within this box. The whiskers of this plot represent the extremes within the group. Dot plot component: Illustrates expression values observed in individual tumor samples. Expression analysis of CD47 across (FIG. 7B) Toronto (FIG. 7C) Boston and (FIG. 7D) Heidelberg datasets shows subgroup-specific expression of CD47. (FIG. 7E) Analysis of CD47 expression across medulloblastoma samples in primary site and metastatic regions. (FIG. 7F) Cell surface expression of CD47 on low passage (<10) primary patient-derived medulloblastoma cell lines as analyzed by flow cytometry. Flow cytometry analysis of CRT on SU-MB002 and D425s cells (FIG. 7G).

(FIG. 9A(i)-(iii)) Representative gating tree to illustrate the process used to select human macrophages for analysis of phagocytosis assay. Gating was done for debris exclusion (far left column), single cell isolation (left middle and middle column), and removal of dead cells (right middle column). Double positive CD14/CD11b cells were gated out to identify human blood-derived macrophages (far right column).

FIG. 10A-10F. Verification of phagocytic activity. (FIG. 10A) Macrophages were identified by their expression of CD14 and CD11b as detected by anti-CD14 and anti-CD11b antibodies, and the tumor cells were loaded with Calcein AM. (FIG. 10B) The populations of cells that was positive for macrophage markers and Calcein (FITC) were sorted out. (FIG. 10C) Wright-Giemsa stain on the sorted cells revealed the engulfment of MB cells by macrophages (scale bar, 50 µm). (FIG. 10D) H&E staining of SU-MB002 xenograft orthotopic tissue treated with Hu5F9-G4 (scale bar, 2 mm). (FIG. 10E) IHC staining for F4/80 protein (a mouse macrophage marker) revealed degraded medulloblastoma cells engulfed by macrophages (scale bar, 100 µm). (FIG. 10F) Higher magnification of (FIG. 10E) (scale bar, 200 µm).

FIG. 11A-11G. Representative tumor burden at treatment initiation. (FIG. 11A) H&E staining of SU-MB002 xenografts at the time of treatment initiation. (FIG. 11A) Cerebellar tumor seen in SU_MB002 xenograft shows leptomeningeal metastasis as well as intraventricular spread 5 d after tumor transplantation (scale bar, 2 mm). Higher magnification of tumor spread in (FIG. 11B) cerebellar pia, (FIG. 11C) pial bars of ventral pons, (FIG. 11D) IVth ventricle (FIG. 11E) and inferior forebrain (scale bar, 100 µm). (FIG. 11F) H&E staining of D425s xenograft, d 5 after transplantation (scale bar, 2 mm). (FIG. 11G) Higher magnification of (FIG. 11F) (scale bar, 100 µm).

FIG. 12A-12Q. Efficacy and dose-dependent response of Hu5F9-G4 in cell line-derived cMYC amplified MB xenografts. (FIG. 12A, FIG. 12G and FIG. 12M) Schematic timeline for study design. (FIG. 12B, FIG. 12H) Bioluminescence imaging from mice orthotopically injected with luciferase-expressing D425 and D283 lines, randomized and treated with Hu5F9-G4 or control. (FIG. 12C, FIG. 12I) Bioluminescence signal declined in Hu5F9-G4-treated versus control groups. (FIG. 12D, FIG. 12J) Significant improvement in survival is seen in Hu5F9-G4-treated mice compared to control group (D; D425, n=10 per group, P<0.0001, log-rank analysis and J; D283, n=10 per group, P<0.0001, log-rank analysis). (FIG. 12E, FIG. 12K) Representative H&E staining of brains from treated and control mice. Local and leptomeningeal tumor spread in control brain (upper panel) versus minimal tumor residue observed in treated brain (lower panel) (scale bars, 2 mm). (FIG. 12F, FIG. 12L) Immunohistochemistry staining of macrophages using the marker F4/80 shows increased macrophage infiltration in treated compared with control groups (scale bars, 50 µm). (FIG. 12M-12Q) D425s, a subclone of D425 cell line, generated aggressive behavior with 100% penetrance of spontaneous spinal metastasis and high morbidity and mortality in xenograft setting. (FIG. 12N) H&E staining shows tumor burden in control brains compared with treated brains (scale bars, 2 mm). (FIG. 12O) IHC staining indicates macrophage involvement in tumor tissues in treated brains with Hu-5F9G4 compared with controls (scale bars, 50 µm). (FIG. 12P, FIG. 12Q) An increase in survival was achieved with Hu5F9-G4 treatment at a higher dose of 450 µg per mouse three times a week (Q, n=5 per group, P<0.0023, log-rank analysis) compared to the standard dosing scale of 250 µg (P, n=5 per group, P<0.0018, log-rank analysis).

(FIG. 13A) Serum concentrations of Hu5F9-G4 in mice engrafted with SU-MB002 and treated every 48 h for 2 weeks with Hu5F9-G4 (100 µg/dose) were determined by ELISA. Serum was collected before treatment and 2 h after treatment with Hu5F9-G4 after the 1st, 2nd, 3rd, and 5th doses. (FIG. 13B) CSF was collected from mice orthotopically xenografted with MB tumor and mice without tumor. The mice were treated with Hu5F9-G4 for 2 weeks before CSF collection. CSF concentrations of Hu5F9-G4 were determined with ELISA test. The concentrations were compared with the relevant values in control mice. (FIG. 13C) The image and sagittal schematic of a mouse brain with clear delineation of the spot for CSF collection. (FIG. 13D) IHC staining with anti-IgG4 antibody showed IgG4 staining in tissues treated with Hu5F9-G4 compared to control group (scale bars, 50 µm).

FIG. 14A-14F. Flow cytometric analysis of myeloid cell infiltration after Hu5F9-G4 treatment. (FIG. 14A) Schematic illustration of experimental design. (FIG. 14B-14F) MB xenografts were treated with either control or Hu5F9G4 for 10 d, and the macrophage population in the tumor area was quantitated by flow cytometry. GFP and luciferase-expressing MB cells were orthotopically implanted in NSG mice. After 10 d of treatment with either control or Hu5F9-G4, the brains were dissected and a sagittal midline section was made. The sagittal sections were visualized under a fluorescent stereomicroscope. GFP fluorescence revealed large primary tumors and leptomeningeal tumor spread in the control brain (FIG. 14B), whereas only localized tumor was observed at the primary cerebellar site with minimal residual leptomeningeal disease in the brain treated with Hu5F9-G4 (scale bars, 5 mm) (FIG. 14D). The GFP-expressing tumors were microdissected and dissociated for flow cytometric analysis. GFP tumor cells were gated out. Within the GFP-(mouse) cells, a significant (P=0.0143) increase in macrophage ($CD14^+$ and $CD11b^+$) was seen in Hu5F9-G4-treated brains (FIG. 14E) compared with the control groups (FIG. 14C). The percentage of recruited macrophages from three brains treated with Hu5F9-G4 compared with three brains from the control cohort (FIG. 14F).

(FIG. 16A) WST-1 assay for evaluation of neural progenitor cell viability after Hu5F9-G4 treatment at different concentrations after 24 h (left panel) and 120 h (right panel). Each colored line represents a different neural progenitor cell line derived from a different fetal specimen. (FIG. 16B) Phagocytosis of differentiated neural cells (neurons and astrocytes) and medulloblastoma cells co-cultured with macrophages and treated with either Hu5F9-G4 or PBS. No significant change was observed in phagocytosis of neurons and astrocytes treated with Hu5F9-G4 compared with their control counterparts, whereas medulloblastoma (P<0.001) and pGBM (P<0.001) cells treated with Hu5F9-G4 show significant engulfment by macrophages in the same experiment.

FIG. 17A-17D. CD47 and calreticulin expression on primary pediatric brain tumor samples. (FIG. 17A) CD47 expression across multiple databases for pediatric glioma, glioblastoma, pilocytic astrocytoma, ATRT, PNET, and ependymoma. Ubiquitous expression of CD47 is seen in all tumors analyzed. There is no significant difference in CD47 expression in tumors compared with normal brain or cerebellum. (FIG. 17B) Flow cytometric analysis of primary patient samples for surface expression of CD47. In most samples analyzed, >80% of the cells expressed CD47 on their surface. (FIG. 17C) Cell surface expression of CD47 in pediatric GBM and DIPG cancer stem cell lines. (FIG. 17D) Cell surface expression of CRT on patient-derived pediatric glioma, ATRT, and normal neural cell lines analyzed by flow cytometry.

(FIG. 18A) Pediatric brain tumor cells from three different pediatric brain tumor types (FIG. 18A) CHB-ATRT1, (FIG. 18B) SU-pGBM001, (FIG. 18C) JHH-DIPGI, (FIG. 18D) SU-DIPGVI) were labeled with Calcein AM and incubated with human peripheral blood-derived macrophages in the presence of 10 μg/nl Hu5F9-G4 or human IgG. Two hours later, the mixed samples were analyzed by flow cytometry to determine the percentage of phagocytosis. P-value was determined using a two-sided t-test.

(FIG. 19A) CD47-positive cells with high expression of nestin. (FIG. 19B) Some CD47-positive cells expressed olig2

FIG. 20A-20D. Efficacy of Hu5F9-G4 in JHH-DIPGI xenografts. (FIG. 20A-20D) In vivo anti-tumor efficacy of Hu5F9-G4 against JHH-DIPGI xenografts. Luciferase-expressing tumor cells were injected in the fourth ventricle (FIG. 20B) and treatment commenced after tumor was detected by bioluminescence imaging. (FIG. 20C) Significant decrease in total flux was observed after 34 weeks of treatment (p=0.0286). (FIG. 20D) Significant increase in survival was observed after Hu5F9-G4 treatment (p=0.006).

FIG. 21A-21G. Contribution of CD47 expression to tumor growth and phagocytosis by macrophages in immunocompetent setting. (FIG. 21A-21F) shRNA-dependent CD47 knockdown in GL261 cells slows down tumor growth in vivo. Analysis of cell surface expression of CD47 in control and CD47 knocked down GL261 by flow cytometry (FIG. 21A). Western blot analysis for total CD47 protein in GL261:CD47-KD cells and control. (FIG. 21B) Study design timeline (FIG. 21C) for mice orthotopically injected with either vehicle or CD47 knocked-down cells, and follow up BLI 15 days after tumor injection (shown in FIG. 21D and quantified in FIG. 21E). Significant extension in survival is seen in mice engrafted with CD47 knocked-down GL261 cell compared to control group (n=7 per group, P=0.0002, log-rank analysis) (FIG. 21F). Immunohistochemical staining with F4/80 antibody showed a notable macrophage presence in tumor tissues from knocked-down CD47 GL261 cells compared to control group (FIG. 21G).

DETAILED DESCRIPTION OF THE EMBODIMENTS

Figure 3A:
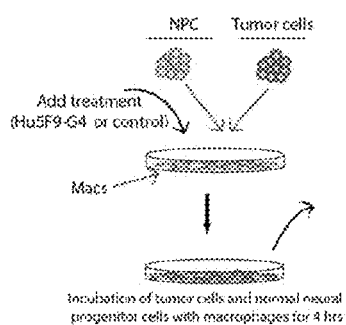
FIG. 3A-3G. Hu5F9-G4 selectively targets tumor cells in vitro and in vivo.
Figure 3B:
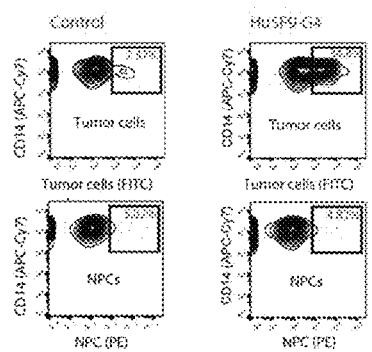
Figure 3C:
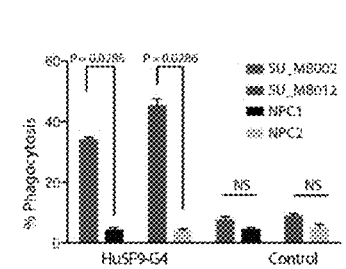

Methods are provided for the targeted depletion of pediatric brain cancer cells in a subject, where the cancer cells are selectively ablated by phagocytosis of the living cells, following contacting with an agent that blocks CD47 signaling.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

Anti-CD47 agent. CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31(2):266-77; Hatherley et al. (2007) J. B. C. 282:14567-75; and the role of SIRPα cis dimerization in CD47 binding is discussed by Lee et al. (2010) J. B. C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

As used herein, the term "anti-CD47 agent" or "agent that provides for CD47 blockade" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent. In an exemplary assay, target cells are incubated in the presence or absence of the candidate agent and in the presence of an effector cell, e.g. a macrophage or other phagocytic cell. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1 2004). Thus, in some embodiments, the anti-CD47 agent does not directly induce cell death of a CD47-expressing cell.

In some embodiments a primer agent is administered prior to administering a therapeutically effective dose of an anti-CD47 agent to the individual. Suitable primer agents include an erythropoiesis-stimulating agent (ESA), and/or a priming dose of an anti-CD47 agent. Following administration of the priming agent, and allowing a period of time effective for an increase in reticulocyte production, a therapeutic dose of an anti-CD47 agent is administered. Administration may be made in accordance with the methods described in co-pending patent application U.S. Ser. No. 14/769,069, herein specifically incorporated by reference.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα.

In some embodiments, a subject anti-CD47 agent is a "high affinity SIRPα reagent", which includes SIRPα-derived polypeptides and analogs thereof (e.g., CV1-hIgG4, and CV1 monomer). High affinity SIRPα reagents are described in international application PCT/US13/21937, which is hereby specifically incorporated by reference. High affinity SIRPα reagents are variants of the native SIRPα protein. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

Optionally the SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

In some embodiments an anti-CD47 antibody comprises a human IgG Fc region, e.g. an IgG1, IgG2a, IgG2b, IgG3, IgG4 constant region. In a preferred embodiment the IgG Fc region is an IgG4 constant region. The IgG4 hinge may be stabilized by the amino acid substitution S241P (see Angal et al. (1993) Mol. Immunol. 30(1):105-108, herein specifically incorporated by reference).

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to the native CD47 sequence.

Continuous delivery device. A continuous delivery device includes, for example, an implanted device that releases a metered amount of an anti-CD47 agent continuously over a period of time. For the methods described herein, the device is generally implanted so as to release the anti-CD47 agent into the cerebrospinal fluid (CSF), into which spaces there is a high probability of pediatric cancer metastasis.

An example of such devices is an osmotic pump, which operates because of an osmotic pressure difference between a compartment within the pump, called the salt sleeve, and the tissue environment in which the pump is implanted. The high osmolality of the salt sleeve causes water to flux into the pump through a semipermeable membrane which forms the outer surface of the pump. As the water enters the salt sleeve, it compresses the flexible reservoir, displacing the test solution from the pump at a controlled, predetermined rate. The rate of delivery is controlled by the water permeability of the pump's outer membrane. Thus, the delivery profile of the pump is independent of the drug formulation dispensed. Drugs of various molecular configurations, including ionized drugs and macromolecules, can be dispensed continuously in a variety of compatible vehicles at controlled rates.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

Antibodies of interest may be tested for their ability to induce ADCC (antibody-dependent cellular cytotoxicity) or ADCP (antibody dependent cellular phagocytosis). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.).

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc. Pediatric humans, e.g. less than about 18 years of age, are of particular interest.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

Pediatric brain tumors. Primary brain tumors are a diverse group of diseases that together constitute the most common solid tumor of childhood. Brain tumors are classified according to histology, but tumor location and extent of spread are also important factors that affect treatment and prognosis. Immunohistochemical analysis, cytogenetic and molecular genetic findings, and measures of proliferative activity are increasingly used in tumor diagnosis and classification.

The classification of childhood central nervous system (CNS) tumors is based on histology and location. Tumors are classically categorized as infratentorial, supratentorial, parasellar, or spinal. Immunohistochemical analysis, cytogenetic and molecular genetic findings, and measures of proliferative activity are increasingly used in tumor diagnosis and classification and will likely affect classification and nomenclature in the future. Primary CNS spinal cord tumors comprise approximately 1% to 2% of all childhood CNS tumors. The classification of spinal cord tumors is based on histopathologic characteristics of the tumor and does not differ from that of primary brain tumors.

Infratentorial (posterior fossa) tumors include the following: Cerebellar astrocytomas (most commonly pilocytic, but also fibrillary and less frequently, high grade); Medulloblastomas (including classic, desmoplastic/nodular, extensive nodularity, anaplastic, or large cell variants); Ependymomas (papillary, clear cell, tanycytic, or anaplastic); Brain stem gliomas (typically diffuse intrinsic pontine gliomas and focal, tectal, and exophytic cervicomedullary gliomas are most frequently pilocytic astrocytomas); Atypical teratoid/rhabdoid tumors; Choroid plexus tumors (papillomas and carcinomas); Rosette-forming glioneuronal tumors of the fourth ventricle.

Supratentorial tumors include the following: Low-grade cerebral hemispheric astrocytomas (grade I [pilocytic] astrocytomas or grade II [diffuse] astrocytomas); High-grade or malignant astrocytomas (anaplastic astrocytomas and glioblastoma [grade III or grade IV]); Mixed gliomas (low- or high-grade); Oligodendrogliomas (low- or high-grade); Cerebral neuroblastomas and pineoblastomas; Atypical teratoid/rhabdoid tumors; Ependymomas (anaplastic or RELA fusion-positive); Meningiomas (grades I, II, and III); Choroid plexus tumors (papillomas and carcinomas); Tumors of the pineal region (pineocytomas, pineoblastomas, pineal parenchymal tumors of intermediate differentiation, and papillary tumors of the pineal region), and germ cell tumors; Neuronal and mixed neuronal glial tumors (gangliogliomas, desmoplastic infantile astrocytoma/gangliogliomas, dysembryoplastic neuroepithelial tumors, and papillary glioneuronal tumors); other low-grade gliomas (including subependymal giant cell tumors and pleomorphic xanthoastrocytoma); and metastasis (rare) from extraneural malignancies.

Parasellar tumors include the following: Craniopharyngiomas; Diencephalic astrocytomas (central tumors involving the chiasm, hypothalamus, and/or thalamus) that are generally low-grade (including astrocytomas, grade I [pilocytic] or grade II [diffuse]); Germ cell tumors (germinomas or nongerminomatous).

Spinal cord tumors include the following: Low-grade cerebral hemispheric astrocytomas (grade I [pilocytic] astrocytomas or grade II [diffuse] astrocytomas); High-grade or malignant astrocytomas (anaplastic astrocytomas and glioblastoma [grade III or grade IV]); Gangliogliomas; Ependymomas (often myxopapillary).

Children with primary brain or spinal cord tumors represent a major therapy challenge that, for optimal results, requires the coordinated efforts of pediatric specialists in fields such as neurosurgery, neuropathology, radiation oncology, pediatric oncology, neuro-oncology, neurology, rehabilitation, neuroradiology, endocrinology, and psychology, who have special expertise in the care of patients with these diseases. For example, radiation therapy of pediatric brain tumors is technically demanding and should be performed in centers that have experience in this area. For most childhood brain and spinal cord tumors, the optimal treatment regimen has not been determined. Survival rates are wide-ranging depending on tumor type and stage. Long-term sequelae related to the initial presence of the tumor and subsequent treatment are common. Debilitating effects on growth and neurologic development have frequently been observed after radiation therapy, especially in younger children. Secondary tumors have increasingly been diagnosed in long-term survivors. Long-term management of these patients is complex and requires a multidisciplinary approach. Recurrence is not uncommon in both low-grade and malignant childhood brain tumors and may occur many years after initial treatment. Disease may occur at the primary tumor site or, especially in malignant tumors, at noncontiguous central nervous system (CNS) sites. Systemic relapse is rare but may occur. At time of recurrence, a complete evaluation for extent of relapse is indicated for all malignant tumors and, at times, for lower-grade lesions. Biopsy or surgical re-resection may be necessary for confirmation of relapse; other entities, such as secondary tumor and treatment-related brain necrosis, may be clinically indistinguishable from tumor recurrence. The determination of the need for surgical intervention must be individualized based on the initial tumor type, the length of time between initial treatment and the reappearance of the lesion, and the clinical picture.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Concomitant administration" of a cancer therapeutic drug, ESA or tumor-directed antibody with a pharmaceutical composition of the present invention means administration with the high affinity CD47 reagent at such time that both the drug, ESA or antibody and the composition of the present invention will have a therapeutic effect. Such concomitant administration may involve concurrent (i.e. at the same time), prior, or subsequent administration of the drug, ESA or antibody with respect to the administration of a compound of the invention. A person of ordinary skill in the art would have no difficulty determining the appropriate timing, sequence and dosages of administration for particular drugs and compositions of the present invention.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

METHODS OF USE

Methods are provided for treating or reducing pediatric brain tumors, in a regimen comprising contacting the targeted cells with one or more agents that that blockades CD47 activity. Such methods include administering to a subject in need of treatment a therapeutically effective amount of the agent of the invention, including without limitation combinations of the reagent with surgery, a chemotherapeutic drug, radiation therapy, monoclonal antibody therapy, immune-oncology therapy, or an ESA.

Effective doses of the agent of the present invention for the treatment of cancer, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage of the agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including gliomas, medulloblastomas, etc. For such purposes an anti-CD47 agent may be delivered to the expected site of metastatic dissemination, e.g. the CSF. Included particularly is the use of ventricular delivery devices.

For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Compositions for the treatment of cancer can be administered by parenteral, topical, intravenous, intratumoral, oral, subcutaneous, intraarterial, intracranial, intraperitoneal, intranasal or intramuscular means. A typical route of administration is intravenous, intratumoral, ventricular, etc. although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the compositions (e.g., anti-EGFR antibodies; anti-CD47 agents, and formulations thereof) of the invention and instructions for use. The kit can further contain a least one additional reagent, e.g. a chemotherapeutic drug, ESA, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose.", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

EXPERIMENTAL

Example 1

Disrupting the CD47-SIRPα Anti-Phagocytic Axis by a Humanized Anti-CD47 Antibody is an Efficacious Treatment for Malignant Pediatric Brain Tumors Morbidity and mortality associated with pediatric malignant primary brain tumors remain high in the absence of effective therapies. Macrophage-mediated phagocytosis of tumor cells via blockade of the anti-phagocytic CD47-SIRPα interaction using anti-CD47 antibodies has shown promise in preclinical xenografts of various human malignancies. We demonstrate herein the effect of a humanized anti-CD47 antibody, Hu5F9-G4, on five aggressive and etiologically distinct pediatric brain tumors: Group 3 medulloblastoma (primary and metastatic), atypical teratoid rhabdoid tumor, primitive neuroectodermal tumor, pediatric glioblastoma, and diffuse intrinsic pontine glioma. Hu5F9-

G4 demonstrated therapeutic efficacy in vitro and in vivo in patient-derived orthotopic xenograft models. Intraventricular administration of Hu5F9-G4 further enhanced its activity against disseminated medulloblastoma leptomeningeal disease. Notably, Hu5F9-G4 showed minimal activity against normal human neural cells in vitro and in vivo, a phenomenon reiterated in an immunocompetent allograft glioma model. Thus, Hu5F9-G4 can be a safe and effective therapeutic agent for managing multiple pediatric central nervous system malignancies.

Based on mechanism of action and potent pre-clinical activity, we hypothesized that pediatric brain tumors would be susceptible to blocking CD47 antibodies. A humanized anti-CD47 antibody with a human IgG4 scaffold (Hu5F9-G4) was engineered to minimize the recruitment of antibody Fc-dependent effector functions and to reduce immunogenicity of the antibody. We tested the anti-tumor activity of Hu5F9-G4 in human patient-derived primary xenograft models from five of the most malignant pediatric brain tumors: Group 3 MB, ATRT, PNET, EGFR-amplified pediatric GBM (pGBM), and diffuse intrinsic pontine glioma (DIPG) harboring histone 3.3 K27M mutation.

Here, we report that Hu5F9-G4 demonstrates potent activity against these primary malignant pediatric brain tumor types, regardless of histologic classification or molecular origin. Furthermore Hu5F9-G4 was highly efficacious against primary tumor and subarachnoid dissemination, with negligible activity against normal neural cells.

Figure 7A:
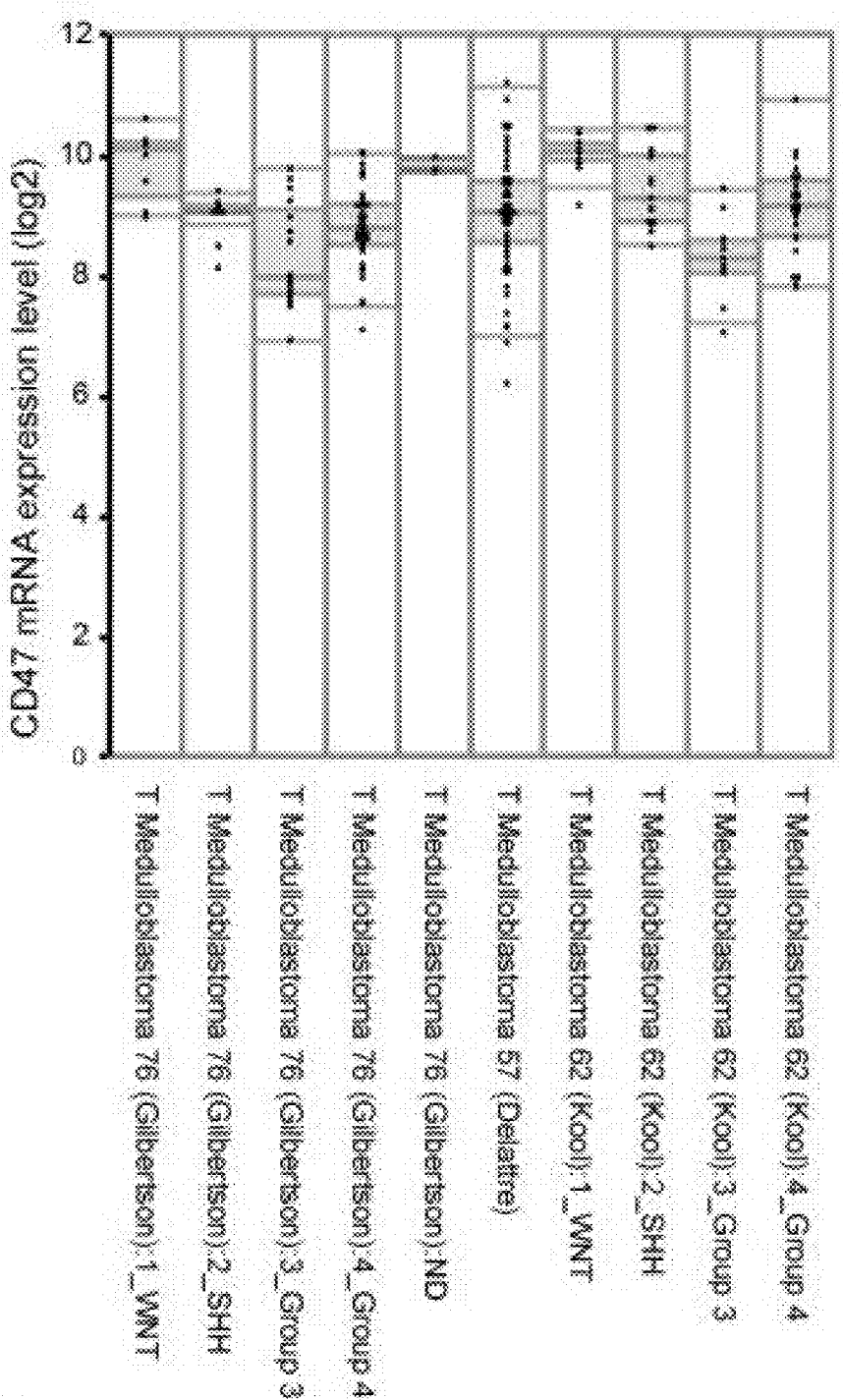
Figure 7E:
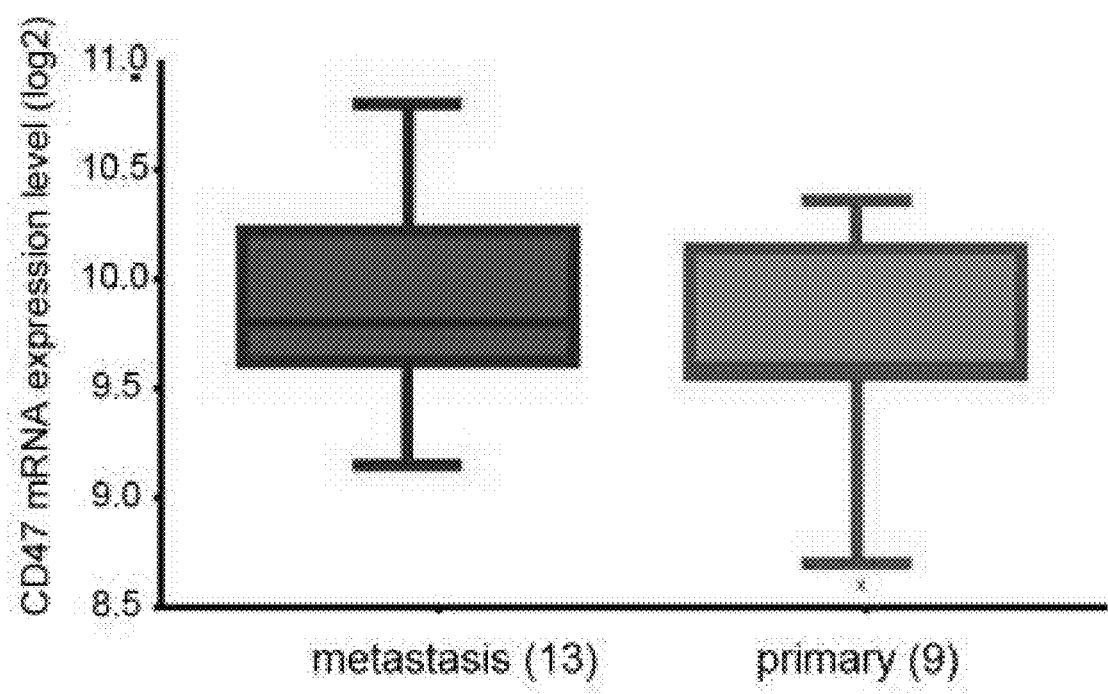
Figure 7F:
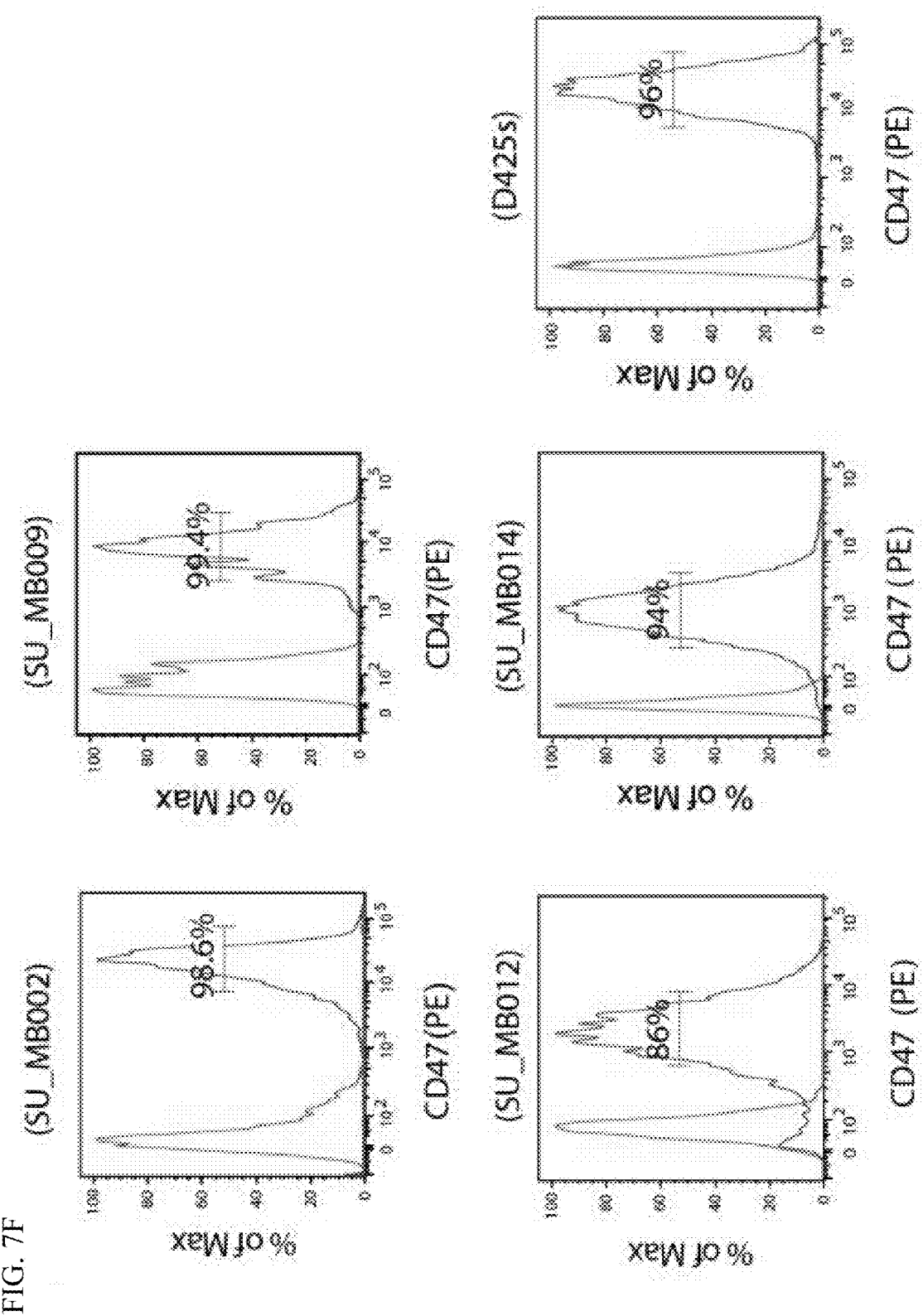
Figure 7G:
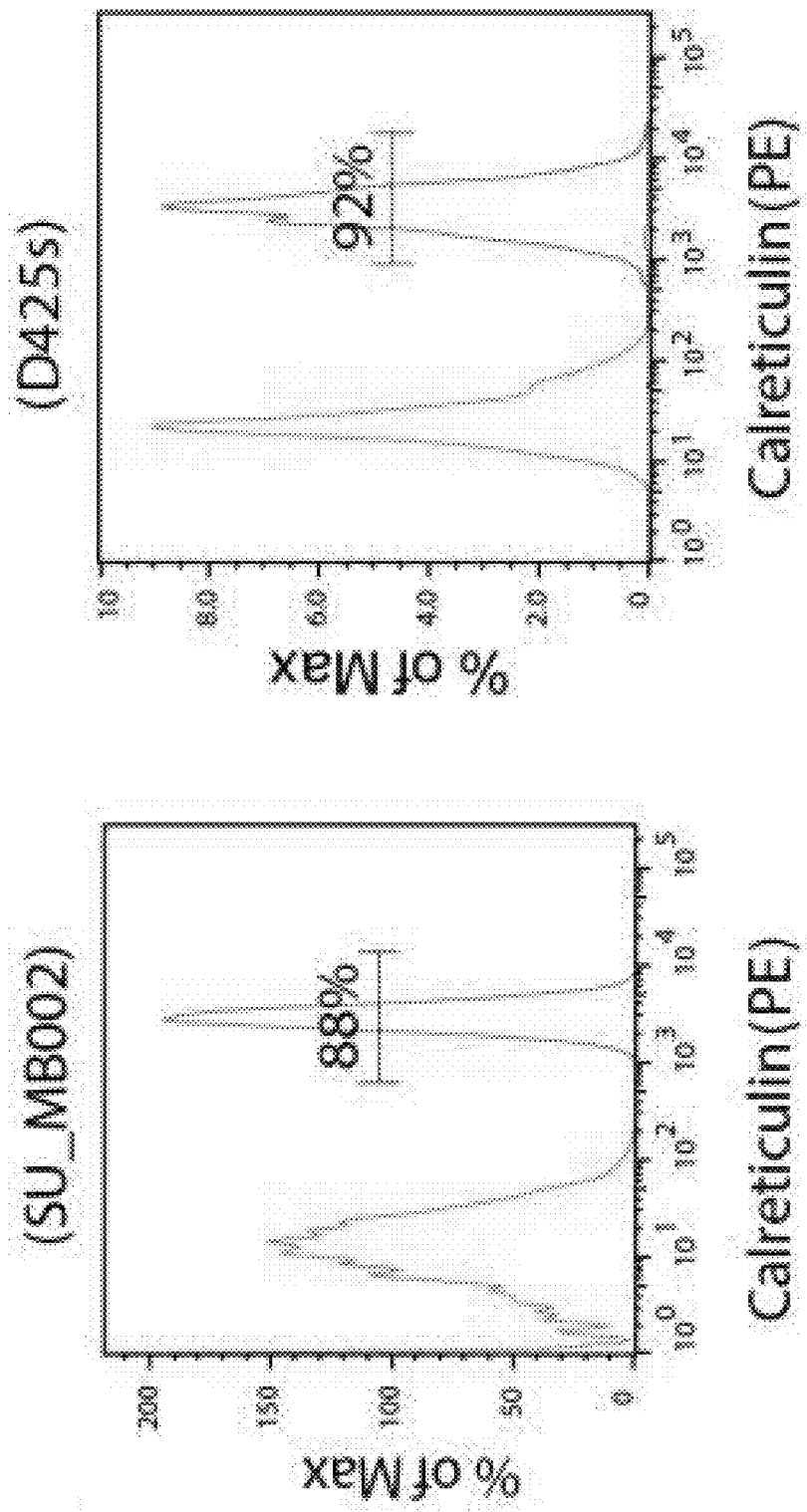
Figure 8A:
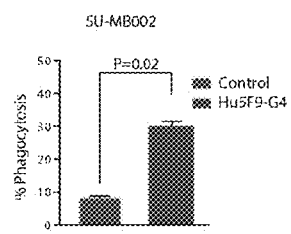
FIG. 8A-8D. Hu5F9-G4 induces potent macrophage-mediated phagocytosis of MB cells derived from surgical specimens. Phagocytosis assay was carried out as described in the Materials and Methods. Calcein AM-labeled tumor cells and macrophages were co-incubated in the presence of Hu5F9-G4 or IgG control. After an incubation period, cells were stained with anti-CD14 and anti-CD11b antibodies and analyzed on a flow cytometer. Macrophages were distinguished from tumor cells as being $CD14^+CD11b^+$. Macrophages with engulfed tumor cells in them were identified as $CD14^+CD11b^+$ Calcein. Efficiency of phagocytosis was calculated as the percentage of macrophages with engulfed tumor cells in them. Data are shown from (FIG. 8A) SU-MB002, (FIG. 8B) SU-MB014, (FIG. 8C) SU-MB012 and (FIG. 8D) D425s MB cells. Cells were subjected to phagocytosis by macrophages from at least two different blood donors.
Figure 8B:
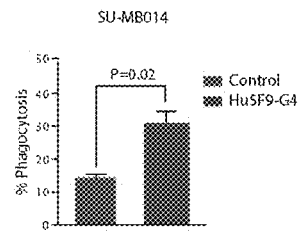
Figure 8C:
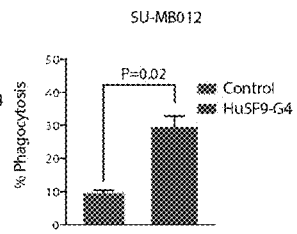
Figure 8D:
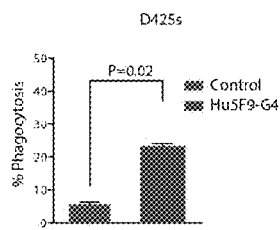

Hu5F9-G4 induces phagocytosis and inhibits growth of human Group 3 MB. MB has been molecularly classified into four core subgroups: WNT, SHH, Group 3, and Group 4. The 5-year overall survival of Group 3, the most aggressive subgroup, is 50%, and approximately 30% in patients presenting with metastases at the time of diagnosis. Ubiquitous expression of CD47 was observed in the Boston, Heidelberg, and Toronto MB gene expression datasets (FIG. 7, A to D). Gene expression analysis suggests higher CD47 expression in metastatic regions of medulloblastoma as compared to the primary site tumor (FIG. 7E). Analysis of CD47 surface expression by flow cytometry on human Group 3 MB tissue specimens showed 86-99.4% of cells expressing CD47 on their surface (FIG. 7F). MB lines also showed cell surface exposure of calreticulin (CRT), a prophagocytic "a eat me" signal, by flow cytometry (FIG. 7G). We therefore hypothesized that blocking the CD47-SIRPα interaction by Hu5F9-G4 will facilitate phagocytosis of Group 3 MB tumors by macrophages, resulting in elimination of the primary tumor as well as metastases.

Figure 9A:
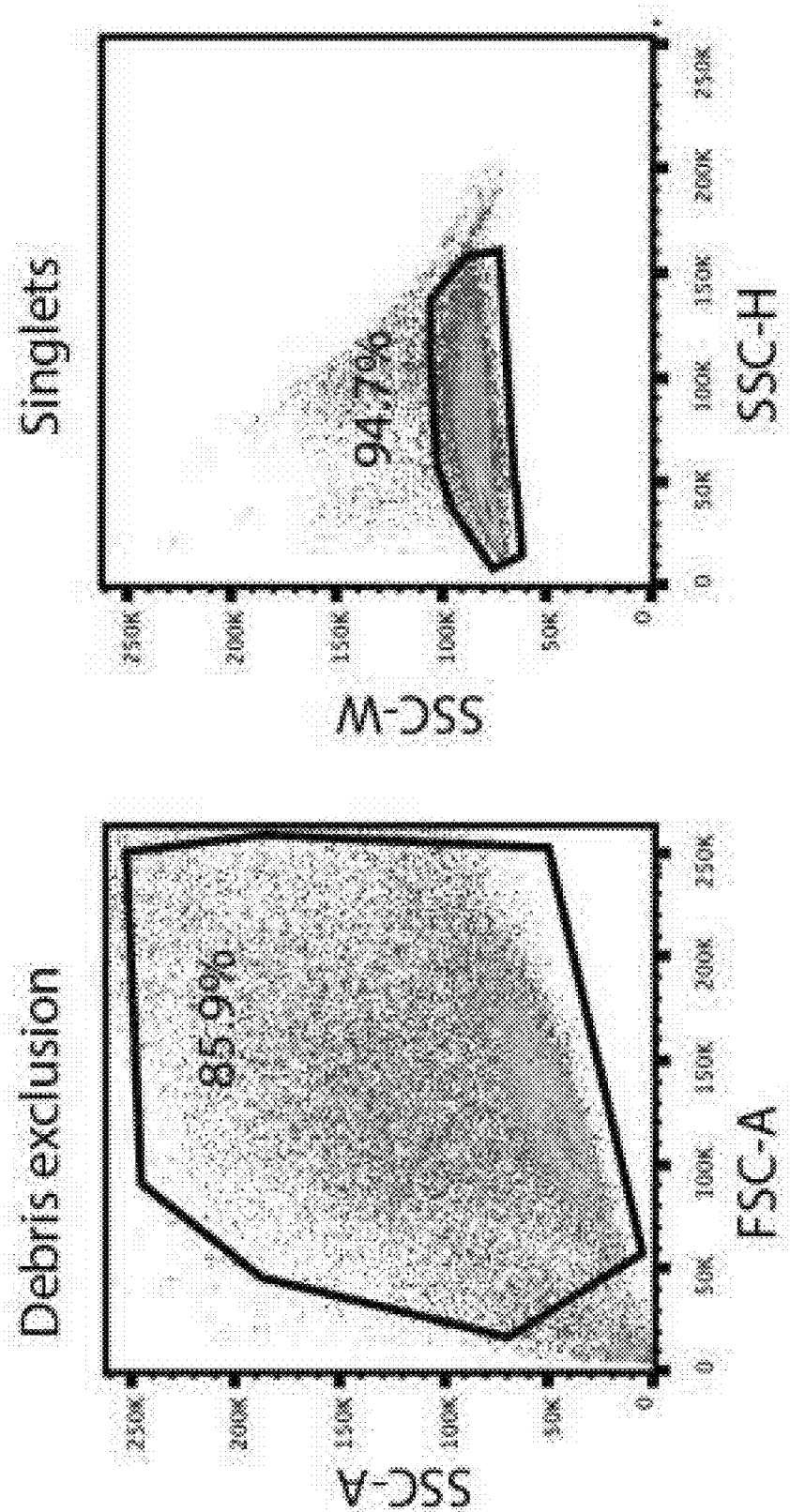
FIG. 9A(i)-9B(ii). Flow cytometry gating strategy.

In vitro phagocytosis assays with human peripheral blood mononuclear cell (PBMC)-derived macrophages established the ability of Hu5F9-G4 to induce phagocytosis of primary and xenograft-derived MB cells (FIG. 8, A to D, and background gating strategy, FIG. 9A,B). The engulfment of tumor cells by macrophages was verified by cell sorting of CD11b$^+$CD14$^+$ Calcein$^+$ cells and subsequent Wright-Giemsa staining after cytospin (FIG. 10, A to C). The administration of Hu5F9-G4 in mice bearing MB promoted extensive in vivo phagocytosis of Group 3 MB cells (FIG. 10, D to F).

We tested the in vivo antitumor effect in an orthotopic xenograft model in immunodeficient NSG mice that lack B, T, and NK cells, but retain macrophages with phagocytic potential. Two primary Group 3 (SU_MB002 and SU_MB009) and three commercial cMYC amplified MB cell lines (D283, D425, and D425s), expressing green fluorescent protein (GFP) and luciferase, were transplanted into the cerebellum of NSG mice. Tumor engraftment was verified by bioluminescence (BLI) imaging of all transplanted mice and by hematoxylin and eosin (H&E) staining of a representative mouse from each group. MB was seen at the primary site (cerebellum) and disseminated to the leptomeninges (FIG. 11, A to G). Intraperitoneal (i.p.) treatment with Hu5F9-G4 was initiated after randomization by BLI flux values to ensure that tumors were of equal size in the treatment and control groups (treatment schemes, FIG. 1A). BLI imaging showed a significant reduction in tumor burden after treatment with Hu5F9-G4 (SU-MB002, P=0.0057) (FIGS. 1, B and C). Kaplan-Meier analysis of mice injected with SU_MB002 showed significant improvement in survival of the Hu5F9-G4-treated cohort compared with the control (P<0.0001) (FIG. 1D).

Tumor burden in treated versus control mice were verified using H&E staining. H&E staining of brains from Hu5F9-G4-treated mice showed no tumor cells or minimal residual tumor in the cerebellum or leptomeninges, whereas control mouse brains harbored large tumors in the cerebellum with extensive leptomeningeal spread (FIG. 1E). To assess tumor cell engulfment by macrophages in vivo, IHC staining was performed on orthotopic xenografted brains treated with either control or Hu5F9-G4. Substantial macrophage recruitment was detected in the group treated with Hu5F9-G4, concentrated around sites of residual tumor upon staining for F4/80, a pan-macrophage marker. However, control animals with substantial tumor burden showed limited but diffuse presence of macrophages (FIG. 1F).

To test the effect of Hu5F9-G4 on multiple primary patient-derived MB lines, a similar set of experiments was conducted using D283, D425, and D425s lines (FIG. 12, A to Q). The tumor cells were transplanted into the cerebellum of NSG mice. Tumor engraftment was verified by BLI imaging, and treatment scheme was determined after randomization (FIGS. 12, A, G, and M). Significant reduction in BLI (P<0.0001) was seen in mice xenografted with D425 and D283 followed by Hu5F9-G4 treatment (FIGS. 12, B-C, and H-I). Mice implanted with D425, D283, and D425s and treated with Hu5F9-G4 showed significant extension in survival (P<0.0001, <0.0001, and 0.0018, FIGS. 12, D, J, and P).

IHC and staining against F4/80 protein were performed on dissected brains after the treatment. A reduced tumor burden and substantial macrophage recruitment were detected in the groups treated with Hu5F9-G4, whereas the control brains showed large tumors with negligible presence of macrophages (FIGS. 12, E-F, KL, and N-O, and table 1).

We tested for dose-dependent effect of the monoclonal antibody in vivo and found that the survival of animals with D425s xenografts was significantly improved by increasing the dose of Hu5F9-G4 from 250 to 450 μg/mouse, 3 times per week (P=0.0023) (FIG. 12Q). Qualitative evaluation of behavior revealed that mice treated with Hu5F9-G4 displayed normal feeding and movement, whereas those treated with the control were cachectic, hunched, and lethargic.

Figure 13A:
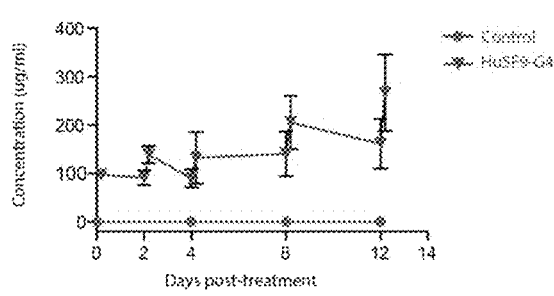
FIG. 13A-13D. Pharmacokinetic analysis and brain penetrance of Hu5F9-G4.
Figure 13B:
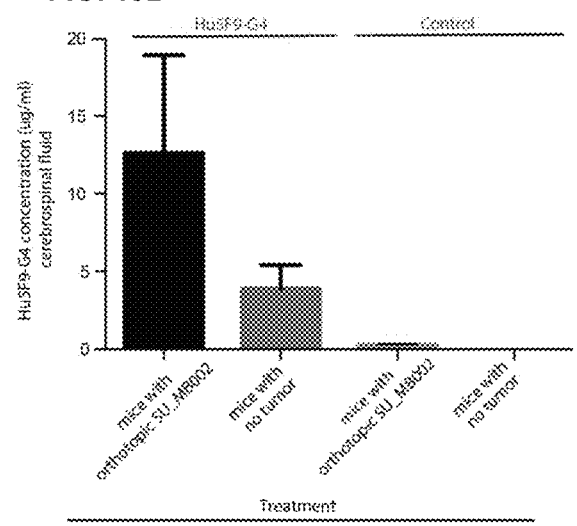
Figure 13C:
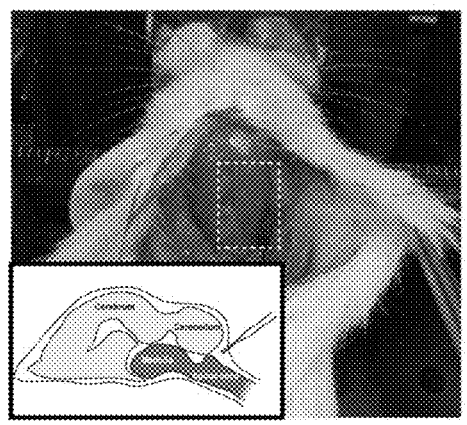
Figure 13D:
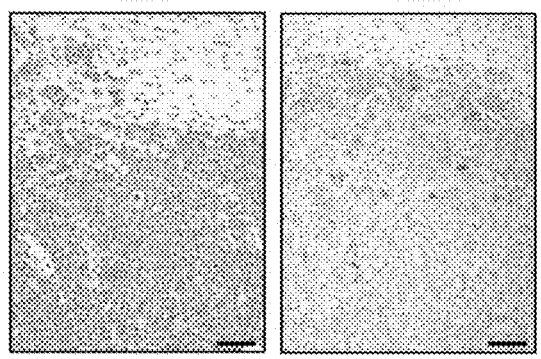

Because metastatic recurrence of MB with MYC amplification has near 100% fatality in children, we tested the effect of Hu5F9-G4 on spinal metastases from MYC amplified Group 3 cell lines. Hu5F9-G4 treatment was able to clear metastases from the spine in this xenograft model (FIG. 1, G to I), thus establishing the efficacy of Hu5F9-G4 treatment in all regions of the CNS. Similar results were seen in D425 xenografted mice, where no spinal metastasis was observed in Hu5F9-G4 treated mice compared with 80% of the mice in the control cohort (FIG. 12B). Furthermore, a therapeutic dose of Hu5F9-G4 administered i.p. was around 200 μg/ml in blood serum and 20 μg/ml in cerebrospinal fluid (CSF), proving penetration of the blood-brain barrier by Hu5F9-G4 (FIG. 13, A to C). Additionally, we detected the presence of Hu5F9-G4 in CSF of non-tumor-bearing mice, establishing its ability to traverse the blood-brain barrier even when no tumor is present (FIG. 13B). IHC staining for IgG4 in the brains of tumor-bearing mice treated with Hu5F9-G4 revealed high staining of IgG4 in the treated group and no sign of staining in the control, further confirming the penetration of Hu5F9-G4 to brain tumor tissue in treated mice (FIG. 13D).

Figure 15:
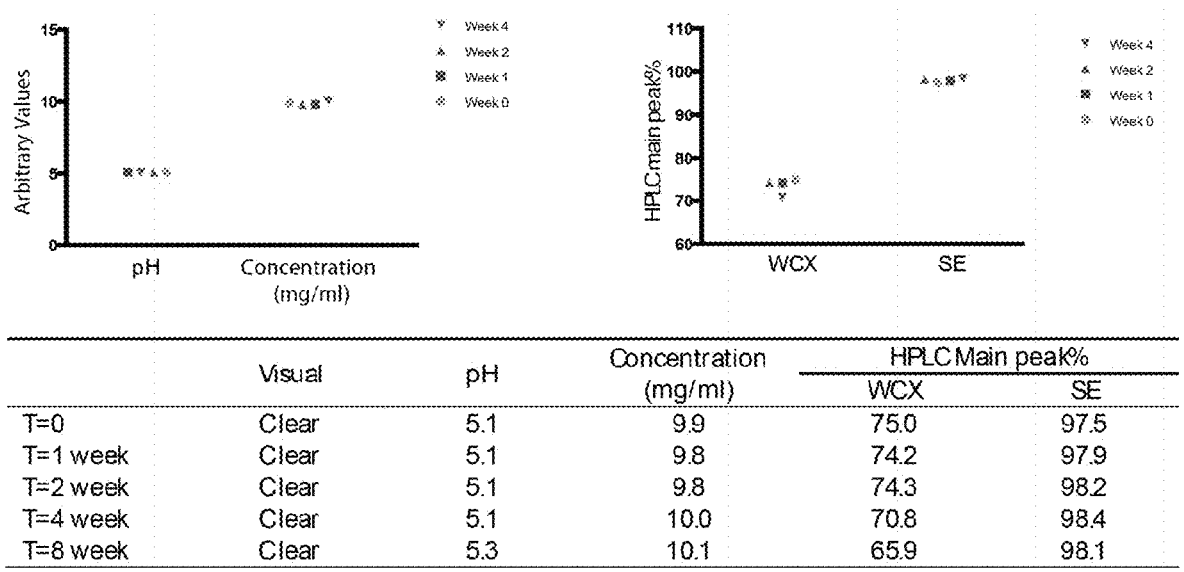
FIG. 15. Stability of Hu5F9-G4. The stability of Hu5F9-G4 was studied by visual inspection, pH measurement, osmolality measurement, absorbance spectrophotometry, SDS-PAGE gel, weak cation exchange HPLC (WCX-HPLC), and size-exclusion HPLC (SE-HPLC). Hu5F9-G4 was stable for at least 2 months when stored at −70° C., 2-8° C. and ambient temperature.

To quantitate the recruitment of macrophages within the tumor area, Hu5F9-G4-treated mice and controls were sacrificed after five injections of Hu5F9-G4 (one injection every other day); brains were extracted and the tumors identified by GFP under a fluorescence stereomicroscope. Engrafted tumors were micro-dissected, dissociated to single cells, and analyzed for the presence of macrophages by the expression of CD11b and F4/80 (FIG. 14, A to F). Flow cytometric analysis showed significantly higher frequency of intra-tumoral macrophages (P: 0.0143) in the treated (15.7%) versus the control (3.32%) groups (FIGS. 14, C, E, and F). Together, these results demonstrate that Hu5F9-G4 treatment crosses the blood-brain barrier and has potent anti-tumor activity against Group 3 MB in vivo. All mice bearing MB cell lines (SU-MB002, D425, D283, D425s, and SU_MB009, FIG. 15, A to E) responded to Hu5F9-G4 treatment with extended survival, less tumor burden, and more macrophages present in the residual tumor versus controls.

Figure 9B:
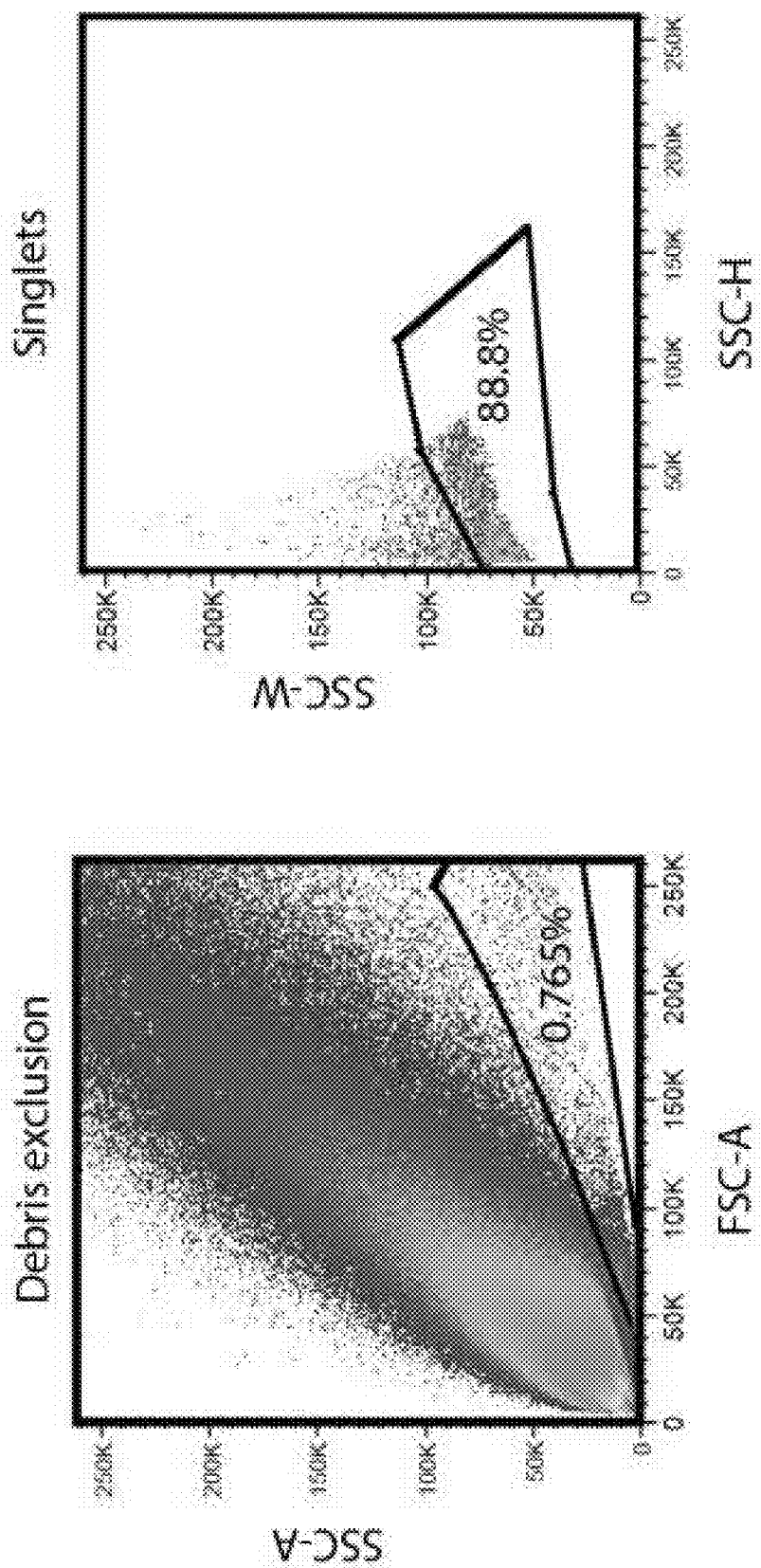
(FIG. 9B(i)-(ii)) Representative sample gating of medulloblastoma xenografts from treated and control mice before brain tumor stem cell analyses. The tumors were dissociated and processed for removing debris (far left column), single cell isolation (left and right column), and purifying live population (far right column). The first SSC-A and FSC-A gate was re-drawn after back-gating for DAPI-(live)/mouse CD45-CD31-H2Kd- (mouse hematopoietic and endothelial lineage cells)/GFP+(human cells).
Figure 10A:
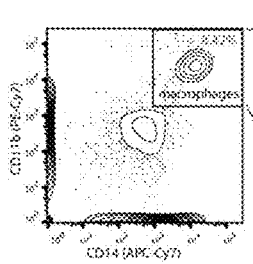
Figure 10B:
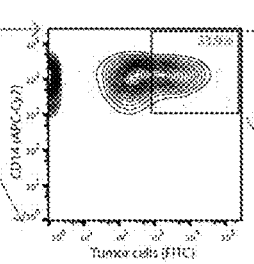
Figure 10C:
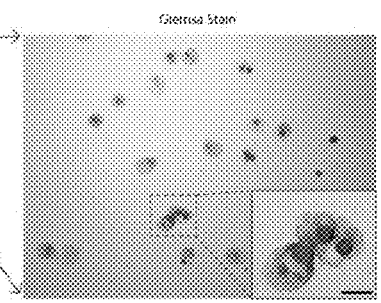
Figure 10D:
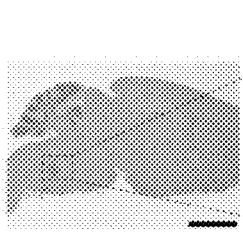
Figure 10D:
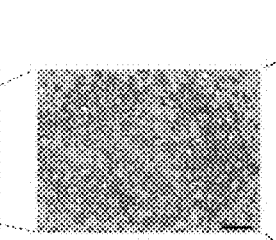
Figure 10F:

Because the growth of MBs depends on $CD15^+$ cancer stem cells (CSCs)(25, 26), we tested the ability of Hu5F9-G4 to target $CD15^+$ MB CSCs. Flow cytometric analysis of MB xenografts 2 d after the $6^{th}$ injection of Hu5F9-G4 treatment showed a lower frequency of human $CD15^+$ cells in the Hu5F9-G4-treated mice than in the controls (P: 0.02) (FIGS. 1, J and K and background gating strategy FIG. 9B). Thus, $CD15^+$ Group 3 MB CSCs are also targeted by Hu5F9-G4 treatment.

Figure 16A:
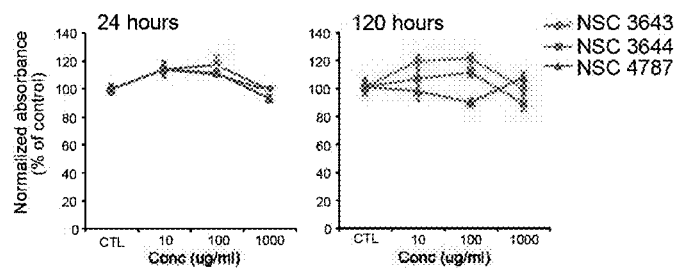
FIG. 16A-16B. Evaluating toxicity of Hu5F9-G4 on human normal neural cells.
Figure 16B:
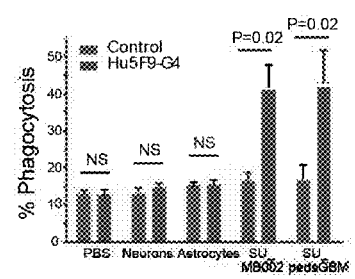

Continuous intraventricular infusion of Hu5F9-G4 inhibits leptomeningeal metastasis of MB. Recurrence of MB is frequently associated with metastasis, and a substantial percentage of Group 3 patients harbor metastatic disease at presentation. Given that MB metastasis typically occurs along the CSF pathways within the leptomeningeal spaces, we wanted to explore the possibility of enhanced targeting of metastatic sites via direct delivery of antibody into the CSF. Mice with cerebellar D425 xenografts presenting with forebrain and spinal metastasis were randomized based on BLI flux values, divided into control and treated groups, and implanted with osmotic pumps delivering 150 μg/day of Hu5F9-G4 to the lateral ventricle via direct cannulation (FIG. 2A). This Hu5F9-G4 dose is comparable to the quantity of antibody received via systemic treatment over the same period. Hu5F9-G4 is stable at ambient temperature for at least 56 d (FIG. 16A). Tumor burden was evaluated by BLI after 14 d of treatment (FIGS. 2, B and C). Intraventricular delivery of Hu5F9-G4 was associated with a significantly longer survival (P: 0.0027) (FIG. 2D); however, this survival advantage was shorter than that associated with systemic treatment (FIG. 12D). Histological analysis of mice with intraventricular treatment showed that, despite elimination of leptomeningeal metastases with increased recruitment of macrophages, the tumor at the primary site was not significantly affected (FIG. 2 E). However, intraventricular delivery of Hu5F9-G4 did provide an accelerated anti-tumor effect on spinal and forebrain leptomeningeal metastases as seen by both histology (FIGS. 2, E and F) and BLI (FIGS. 2, G and H) when compared with systemic treatment. Mice were weighed before and after treatment, and no weight loss was observed in mice treated with intraventricular delivery of Hu5F9-G4 compared with the control (FIG. 2I). These results revealed increased potency of Hu5F9-G4 against leptomeningial disease with intraventricular administration to the CSF, but little to no effect on the primary tumor at the cerebellum, indicating that these two locations have separate barriers to Hu5F9-G4 penetration.

Hu5F9-G4 eliminates MB cells but not normal human CNS cells in a treatment model. Current regimens of radiation and chemotherapy cause considerable and often permanent side effects due to their toxicity to normal cells, particularly to a child's developing brain. Thus, we assessed if Hu5F9-G4 results in any toxicity to human-derived neural cells. No loss in viability or proliferation was observed in normal human neural progenitor cells (NPCs) after 5 d of treatment with Hu5F9-G4 at a concentration as high as 1 mg/ml (FIG. 17A). Furthermore, Hu5F9-G4 failed to induce phagocytosis of normal human NPCs or their differentiated progeny, namely neurons and astrocytes (FIG. 17B).

To further examine whether Hu5F9-G4 could differentiate between tumor and normal cells while selectively targeting cancer cells, we co-incubated tumor cells and normal human NPCs and exposed the combination to Hu5F9-G4 in the presence of human PBMC-derived macrophages (FIG. 3A). Flow cytometric analysis revealed 7-fold higher phagocytosis of tumor cells compared with phagocytosis of NPCs (FIGS. 3, B and C). In fact, the phagocytosis of NPCs was not above background levels even in the presence of active phagocytosis of tumor cells in vitro.

Figure 3D:
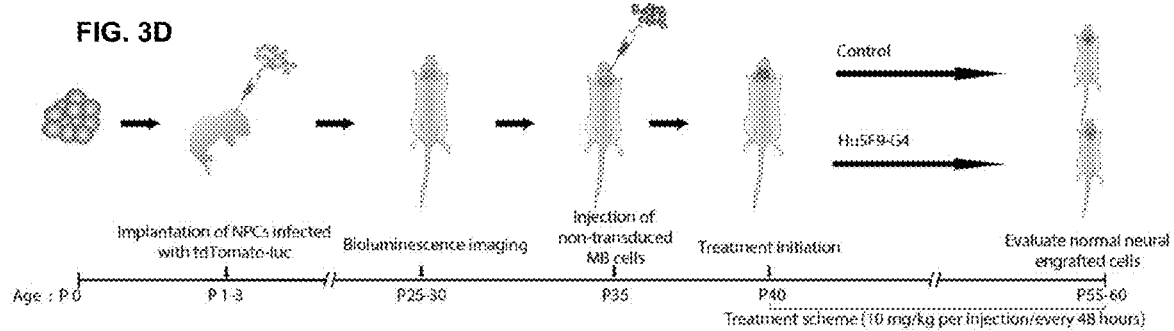
Figure 3E:
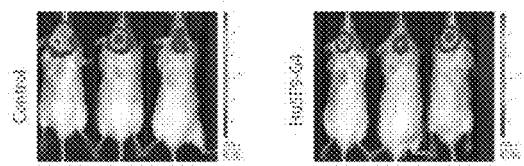
Figure 3F:
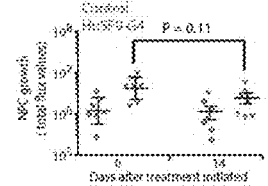
Figure 3G:
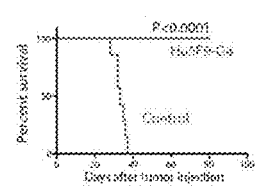

To determine whether Hu5F9-G4 has an in vivo bystander effect on normal human NPCs, we developed a surrogate assay. Previously, we had demonstrated the ability of human fetal brain-derived NPCs to engraft into NSG mouse brains and migrate and differentiate in a site-appropriate fashion into neurons, astrocytes, and oligodendrocytes. Using this model, non-transduced human MB cells (SU_MB002) were injected into mice that had previously been engrafted with luciferase-expressing human neural precursor cells. These mice, harboring both human tumor and normal human CNS cells, were then treated with Hu5F9-G4 or the control (FIG. 3D). In this case, BLI signal was observed and measured from the engrafted normal human NPCs and their progeny cells and not from the tumor cells. No significant change was observed in BLI signal after treatment with Hu5F9-G4, suggesting robust and continued cellular proliferation and viability even in the presence of Hu5F9-G4 treatment (FIGS. 3, E and F). The anti-tumor activity of Hu5F9-G4 was confirmed by Kaplan-Meier survival analysis (FIG. 3G). Therefore, little if any elimination of normal human CNS cells was observed in the setting of potent in vivo antitumor activity of Hu5F9-G4 against MB cells.

Figure 18A:
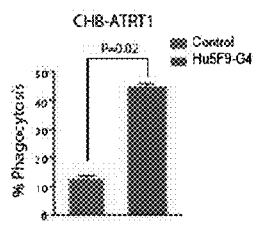
FIG. 18A-18D. Macrophage-mediated phagocytosis of pediatric brain tumor cells.
Figure 18B:
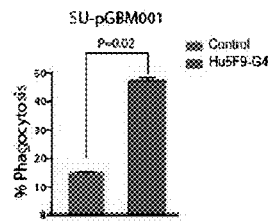
Figure 18C:
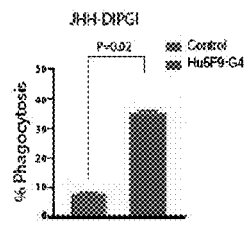
Figure 18D:
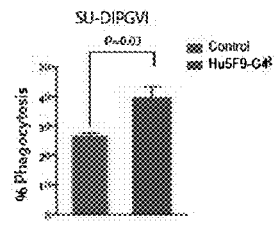
Figure 19A:
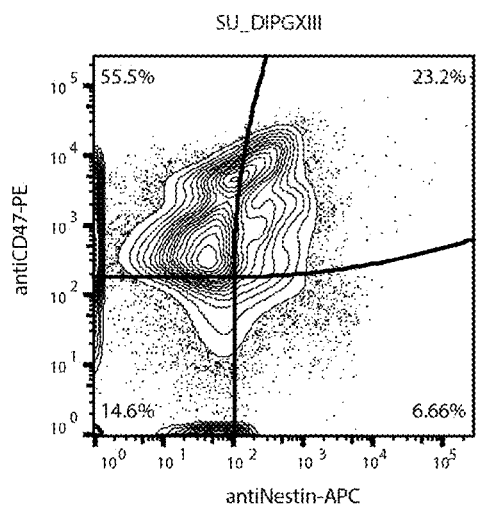
FIG. 19A-19B. High expression of olig2 and nestin on CD47 positive DIPG cells.

Hu5F9-G4 induces phagocytosis and inhibits growth of human pediatric ATRT and PNET xenografts. ATRT and PNET are highly malignant pediatric brain tumors with poor prognosis. We hypothesized that CD47 is expressed on the surface of ATRT and PNET cells and that Hu5F9-G4 treatment would enable the phagocytosis of these tumor cells. Expression analysis of the limited dataset available (n=18) showed CD47 expression in all ATRT tumors (FIGS. 18, A and B). Flow cytometric analysis of ATRT and PNET primary cell lines derived from patient surgical samples showed surface expression of CD47 and CRT on almost all cells (FIGS. 4, A, B and FIGS. 18 C and D). The normal neural stem cell lines expressed a negligible amount of CRT on the cell surface, suggesting the specificity of this marker as a pro-phagocytic "eat me" signal on cancer cells (FIG. 18D). Similarly, fresh frozen surgical samples exhibited widespread expression of CD47 in both tumor types by immunofluorescence staining (FIGS. 4, C and D). In vitro phagocytosis of both tumor types was approximately 5-fold higher upon treatment with Hu5F9-G4 versus controls (FIG. 4E and FIG. 19A). We intracranially transplanted GFP- and luciferase-expressing ATRT or PNET cells into NSG mouse brains and started treatment after tumor engraftment was verified by BLI imaging. Subsequent i.p. treatment (treatment scheme FIG. 4F) of SU_ATRT002 xenografts with Hu5F9-G4 resulted in a significant reduction in tumor growth and possible elimination of the tumor in some mice compared with the controls as observed by BLI (P<0.0001) (FIGS. 4, G and H). Kaplan-Meier analysis demonstrated increased overall survival of mice treated with Hu5F9-G4 compared with controls (P value<0.0001) (FIG. 4I). H&E staining of brains xenografted with ATRT showed reduced tumor burden in the treated group compared with controls (FIG. 4J). Immunohistochemical staining with the macrophage marker F4/80 indicated increased infiltration of macrophages at the tumor site in treated cohorts versus control (FIG. 4K). These results indicate that Hu5F9-G4 has extensive in vitro and in vivo activity against ATRT.

Similarly, to test the efficacy of Hu-5F9G4 against PNET tumors, intracranial xenografts of luciferase-expressing PNET cells were randomized based on BLI into treatment and control groups (FIG. 4L). BLI flux analysis after 28 days of treatment revealed a significant decline in tumor burden of mice treated with Hu-5F9G4 (P=0.0079) (FIG. 4M-N). Subsequent survival analysis showed the extended survival in a treated group with Hu-5F9G4 (P<0.001) (FIG. 4O). H&E staining of brains xenografted with PNET revealed minimal tumor burden in mice treated with Hu-5F9G4 (FIG. 4P). IHC staining against F4/80 protein showed the increased entrance of macrophages into the tumor site in Hu-5F9G4 treated mice (FIG. 4Q).

Figure 19B:
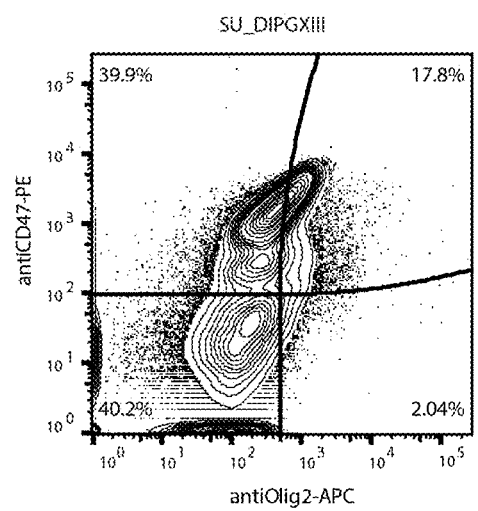

Hu5F9-G4 induces phagocytosis and inhibits tumor growth of human pGBM and DIPG. Pediatric high-grade gliomas (pHGG) are deadly tumors and include pGBM and DIPG. pGBM has a median survival of 5 years, with few patients responding to current treatments. Children with DIPG usually succumb to disease in less than 1 year from diagnosis. We hypothesized that CD47 is highly expressed on pGBM and DIPG, and that using Hu5F9-G4 to block CD47 on the cell surface of pGBM or DIPG would enable the phagocytosis of pediatric glioma cells, resulting in an inhibition or elimination of the tumor. To evaluate the expression of CD47 in pHGG, we interrogated multiple published gene expression datasets for CD47 expression. All datasets indicated ubiquitous expression of CD47 in pGBM and DIPG (FIGS. 18, A and B). Pediatric glioma initiating cell (PGIC) lines derived from either postmortem DIPG rapid autopsy samples (SU_DIPGVI, SU_DIPGXIII, and JHH_DIPGI) or patient surgical pGBM samples (SU_pGBM001 and SU_pGBM002) showed high expression of CD47 by flow cytometry analysis (FIGS. 5, A and B, and FIG. 18C). Furthermore, flow cytometry analysis showed surface expression of CRT on pGBM and DIPG cells (FIG. 18D). Immunofluorescence staining of fresh frozen patient samples showed expression of CD47 in primary tumors (FIGS. 5, C and D). Using flow cytometry (gating strategy shown in FIG. 9A), we evaluated the ability of Hu5F9-G4 to induce the phagocytosis of dissociated primary PGICs in vitro. In contrast to PGICs treated with human IgG, PGICs treated with Hu5F9-G4 were efficiently phagocytosed by macrophages derived from PBMCs (FIG. 5, E to H, and FIG. 19, B to D). We further observed co-expression of the neural/tumor progenitor markers, Olig2 and Nestin with CD47 (FIGS. 20 A and B). We intracranially transplanted GFP- and luciferase-expressing SU-pGBM002 cells into NSG mouse brains and started treatment after tumor engraftment was verified by BLI imaging (treatment scheme FIG. 5I). Intraperitoneal treatment with Hu5F9-G4 resulted in a significant reduction in tumor growth, with elimination of the tumor in SU_pGBM002 (P value: 0.0003) (FIGS. 5, J and K). Mice treated with Hu5F9-G4 showed significant survival benefit compared to control counterparts (P value<0.0001) (FIG. 5L). H&E staining showed reduced tumor burden (FIG. 5M), and IHC staining against the macrophage marker F4/80 indicated increased infiltration of macrophages in Hu5F9-G4-treated cohorts versus controls (FIG. 5N). GFP- and luciferase-expressing SU-DIPGXIII and JHH_DIPGI cells were injected into the pons of NSG mice, and after verification of engraftment with BLI imaging, the mice were randomized for treatment trial (treatment scheme FIG. 5O and FIG. 21A). Significant reduction in SU-DIPGXIII and JHH_DIPGI burden was shown by BLI measures 50 and 28 days after treatment initiated with HU5F9-G4 (P value<0.0001, 0.0286) (FIGS. 5, P and Q, and FIGS. 2I, B and C). Survival analysis revealed a significant survival extension in treated mice with HU5F9-G4 compared to the control group (P value<0.0001, 0.0069) (FIG. 5R, and FIG. 21D). Fluorescence stereomicroscopy of SU_DIPGXIII-GFP xenotransplanted mouse brains showed high infiltration of GFP-expressing cells in the pons of the control mice (FIG. 5S, upper panel) compared with a minimal presence of tumor cells in the treated group (FIG. 5S, lower panel). These results indicate that Hu5F9-G4 has extensive in vitro and in vivo activity against pGBM and DIPG, two of the deadliest pediatric brain tumors.

Anti-mouse CD47 monoclonal antibody inhibits tumor growth and prolongs survival in immunocompetent syngeneic model. We next tested the safety and efficacy of targeting the CD47-SIRPα axis in mice with an intact immune system. We used a well-characterized mouse high-grade glioma cell line, GL261. GL261 cells treated with anti-mouse CD47 mAb (clone MIAP410: mCD47 mAb) were efficiently phagocytized by bone marrow macrophages derived from C57BL/6 mice, in contrast to GL261 cells treated with IgG alone (FIGS. 6, A and B). An in vivo study was performed by orthotopically implanting GL261 cells into the brains of C57BL/6 mice. After implantation with GL261 luciferase-expressing cells, tumor engraftment was confirmed by BLI. Mice were randomized into mCD47 mAb-treated (16 mg/kg daily) and control groups (treatment scheme FIG. 6C). Tumor growth assessed on day 10 and day 23 of treatment demonstrated a lower rate of tumor growth in treated mice versus the control group (FIGS. 6, D and E). Whereas mice in the control cohort had a median survival of 21 d, mice treated with mCD47 mAb had a prolonged median survival of 32 d (FIG. 6F). A dose-dependent response was seen when the antibody was increased to 32 mg/kg compared with 16 mg/kg of mCD47 mAb, with median survival of the mice receiving the higher dose increased to 38 d (FIG. 6F). We confirmed lower tumor burden in the mCD47 mAb-treated cohort by H&E staining (FIG. 6G) and increased accumulation of peritumoral macrophages by F4/80 staining compared with the control group (FIG. 6H). To assess the toxicity of mCD47 mAb on GL261 allografted mouse brains, we stained the brains with cresyl violet (Nissl) (FIG. 6I) and performed IHC against glial fibrillary acidic protein (GFAP) (FIG. 6J) to characterize neurons and astrocytes, respectively. Normal brain tissue surrounding the tumor revealed no damage to neurons or astrocytes and no signs of gliosis in the treated brains (FIGS. 6, I and J, lower panels) compared with controls (FIGS. 6, I and J, upper panels), as determined by blinded analysis with a board certified neuropathologist. Therefore, the disruption of the CD47-SIRPα axis in a fully immunocompetent setting resulted in antitumoral effects against a mouse malignant glioma allograft.

To investigate the contribution of CD47 expression to tumor growth, we knocked down CD47 in GL261 cells using a mouse CD47shRNA (GL261:CD47-KD). Reduction in cell surface CD47 by shRNA was confirmed by flow cytometry (FIG. 22A) and total CD47 protein content was assayed by western blot analysis (FIG. 22B). In vivo BLI revealed significantly reduced tumor growth (FIGS. 22 C, D, and E) and increased survival (FIG. 22F) in mice transplanted with GL261:CD47-KD cells compared to control (P: 0.0002). Furthermore, immunohistochemical staining for F4/80 showed increased presence of macrophages in mouse brains with GL261:CD47-KD cells compared to control GL261 cells (FIG. 22G).

The treatment of malignant pediatric brain tumors remains suboptimal, particularly in instances in which irradiation and intensive chemotherapy are not viable options, especially in children younger than 3 years of age. In the case of pediatric thalamic GBM and DIPG, tumor resection itself is not an option due to the surgically challenging anatomic location. Furthermore, successful clinical intervention in pediatric patients comes at a price that may include white and gray matter abnormalities, microvascular occlusions, demyelination, and calcifications, any of which can cause serious complications and permanent neurologic and cognitive deficits. Hence, there is a critical need for therapies that minimize the effects on the developing brain of a child. Due to disparate tolerability and pharmacokinetics of pharmaceutical agents between adult and pediatric patients, as well as the different biology of pediatric brain tumors, we conducted an extensive preclinical in vitro and in vivo analysis of Hu5F9-G4 against five different types of malignant pediatric brain tumors. We observed ubiquitous expression of CD47 on the cell surface in all malignant pediatric brain tumors tested by flow cytometry and by immunofluorescence staining of tissue sections. Hu5F9-G4 robustly induced phagocytosis by both human and mouse macrophages in all pediatric malignant primary brain tumors tested. Hu5F9-G4 reduced tumor burden and prolonged overall survival of Group 3 MB, ATRT, PNET, pGBM, and DIPG patient-derived orthotopic xenograft models.

In the case of MB, systemic treatment with Hu5F9-G4 was effective not only against the primary site but also against leptomeningeal forebrain and spinal metastasis. Direct delivery into the CSF accelerated the anti-tumor effect on disseminated metastatic disease both in the forebrain and in the spine. In the majority of patients with MB, most of the primary tumor is removed by surgery. However, recurrence most often occurs by metastatic leptomeningeal dissemination, which is impossible to treat surgically. The tendency to have metastasized at presentation and recur after treatment is more pronounced in the Group 3 (cMYC-driven) subtype. Our results demonstrate potent antitumoral activity of Hu5F9-G4 against leptomeningeal disease when delivered i.p., and an even greater clearance of this spread when the treatment was delivered directly into the CSF. It is possible that direct ventricular delivery of Hu5F9-G4 with or without systemic administration for treatment of patients with advanced metastatic disease may prove more efficacious in the clinical setting. Furthermore, we observed a remarkable decrease in $CD15^+$ tumor-initiating MB cells after Hu5F9-G4 treatment, suggesting Hu5F9-G4 as a viable therapeutic agent for eliminating cancer stem cells and potentially preventing tumor relapse.

We carried out detailed evaluation of Hu5F9-G4 activity towards normal human CNS cells, including proliferating neural progenitors (which would be present in developing pediatric patients). We show a tumor-specific effect, with minimal direct or bystander toxicity towards non-neoplastic cells in vitro and in vivo, similar to our previous studies where blocking anti-CD47 antibodies reduced tumor burden in xenograft models of human leukemias and lymphomas with little to no reduction of hematopoietic stem and progenitor cells. These findings in pediatric brain tumors and hematologic malignancies are consistent with the hypothesis that malignant cells express both "eat me" and "don't eat me" signals on the cell surface. Blocking the "don't eat me" signal results in elimination of tumor due to the dominance of the "eat me" signals. In contrast to cancer cells, normal cells have no or minimal "eat me" signals; therefore, blocking the "don't eat me" signal leaves most of these cells unaffected.

Even though CD47 is highly expressed on tumor cells, there are varying degrees of expression on normal cells, raising the concern of decreased potency due to an antibody sink and potential toxicity. However, here we demonstrate that treatment of mouse glioma orthotopic allografts with anti-mouse CD47 monoclonal antibody (mCD47 mAb) in an immunocompetent model produced an effective antitumor response and prolonged survival with no sign of toxicity as shown previously.

The direct mechanism of antibody transport through the blood brain barrier is unknown; however, our results show positive anti-IgG4 (corresponding to IgG4 Fc isotype of Hu5F9-G4) staining in the tumor tissue bed, corroborating the effective infusion of Hu5F9-G4 in treated brains. Growing evidence suggests that the CNS is immunocompetent and interacts dynamically with the systemic immune system. The blood brain barrier itself can be compromised by malignant brain tumors, which allows for increased entry of antibodies. During inflammation, immune cells migrate into the parenchyma by chemotaxis, traveling through cytokine gradients induced by IFN-γ, a key pro-inflammatory myeloid activator, among others. Moreover, FcRn, a ubiquitous immunoglobulin receptor highly expressed in blood vessels in the brain, can facilitate IgG transport into the CNS. All these mechanisms point toward antibody-based immune therapies as a viable option against malignant brain tumors.

Currently, next generation immunotherapies such as checkpoint inhibitors and other regulators of adaptive immune responses are in trials for various cancers. It is possible that tumor phagocytosis in vivo will reflect the in vitro demonstration that macrophages can cross-present class I tumor peptides to CD8 T cells, stimulating cell division and maturation to killer T cells. Thus, activation of macrophage phagocytosis with the facilitation of anti-CD47 antibodies may result in direct therapeutic benefit, but may also re-stimulate antitumor T cells, which alone or with checkpoint inhibitor antibodies could improve the outcomes in children with malignant brain tumors.

Although CD47 blockade has shown promising potential against brain tumors, in many cases it does not completely eliminate tumors. This could be due to pharmacokinetic limitations, because penetrance of antibodies decreases with molecular weight. Furthermore, cancer specimens intrinsically differ in their susceptibility to phagocytosis, and CD47 blockade or knockout is not sufficient to induce phagocytosis, but requires an additional pro-phagocytic stimulus, such as opsonizing antibodies and surface exposure of CRT. An additional limitation of this study is the use of immunocompromised xenograft models, which lack B cells, T cells, and NK cells.

Materials and Methods

Study design. The Objective of this study was to determine the preclinical efficacy of Hu5F9-G4 as an effective treatment against malignant pediatric brain tumors. Flow cytometry and immunofluorescent staining was utilized to evaluate surface expression of CD47 on tumor tissues. In-vitro phagocytosis assays by flow cytometry or immunofluorescence were carried out by using cell lines from different pediatric brain tumors as targets and human PBMC or mouse bone marrow derived macrophages as effector cells. Human PBMC were utilized from at least three different donors against each cell line. Tumor formation was monitored by BLI on IVIS spectrum (Caliper Life Science) and quantified with Living Image 4 software, PerkinElmer. The mice were excluded if no tumor engraftment was detected. Based on preliminary pilot experiments for each type of tumor xenograft, we estimated the sample size to ensure adequate statistical power. To allocate animals to experimental groups, BLI was measured from region-of-interest (ROI) using Living Image 4 software, and the animals were randomized with www.randomizer.org. All in vivo experiments were repeated at least 2 times. Blinding was not performed. Mice were euthanized to test tumor burden and macrophage recruitment in-situ. Pharmacokinetic and brain penetrance of Hu5F9-G4 in brain, blood and CSF was measured. To assess toxicity of Hu5F9-G4 a sequential xeno-transplant model was developed and in-situ analysis of tissue was carried out after treatment with Hu5F9-G4. All in vivo experiments were repeated at least 2 times, unless it was mentioned otherwise.

Statistical analysis. All statistical analyses were performed using GraphPad Prism 6 software. Results were expressed as mean+/−SD. Mann-Whitney test was used for group comparisons (two-tailed). Survival analysis was performed using log-rank test. $P<0.05$ was considered significant.

Bioinformatics analysis. Using R2 software and the megasampler function, we compared CD47 mRNA expression patterns in various gene expression profiling studies including brain tumor (n=861) and normal samples (n=225). In a second analysis, we delineated CD47 mRNA expression in MBs (n=195). Subgroup-specific gene expression profiling differences were determined in three gene expression profiling studies including independent MB cohorts. The following data sets were analyzed for CD47 mRNA expression across various types of pediatric brain tumors and normal brain samples: Toronto (GEO ID: GSE21140), Heidelberg (GEO ID: GSE28245), Boston (courtesy: Yoon-Jae Cho), MAGIC (GEO ID: GSE37382), Kool (GEO ID: GSE10327), and Gilbertson (GEO ID: GSE37418).

TABLE 1

Quantitative immunohistochemical assessment of macrophage infiltration in vivo

| Tumor xenograft | Qualitative assessment of F4/80 staining (scale of 1 to 5) | | Percent nuclei (eosin stain) surrounded by F4/80+ cytofilaments at tumor site | |
|---|---|---|---|---|
| | Hu5F9-G4 | Control | Hu5F9-G4 | Control |
| SU_pGBM002 | 3 | 1 | 80% | 9% |
| SU_ATRT002 | 5 | 0 | 90% | 10% |
| sPNET | 5 | 0 | 90% | 8% |
| SU_MB002 | 5 | 1 | 80% | 11% |
| SU_MB009 | 4 | 1 | 50% | 10% |
| D283 | 4 | 0 | 70% | 5% |
| D425 | 4 | 0 | 60% | 10% |
| D425s | 5 | 1 | 80% | 9% |
| GL261 | 4 | 1 | 60% | 20% |

TABLE 2

General characteristics of cell lines used in the study

| Cell line | Age at diagnosis (years) | Gender | Primary resection/ Post therapy | Site of resection | Known mutations/ Subgroups | Number of injected cells in vivo |
|---|---|---|---|---|---|---|
| SU_pGBM001 | | | | | | 80,000 |
| SU_pGBM002 | 12 | Male | Primary resection | | p53, EGFR amplification | 80,000 |
| SU_DIPGVI | 7 | Female | Post Therapy | | H3.3 K27M | |
| SU_DIPGXIII | 6 | Female | Post Therapy | | H3.3 K27M | 100,000 |
| JHH-DIPG-1 | | | Obtained at autopsy | | | 100,000 |
| CHB-ATRT1 | 1 | Female | Primary resection | Posterior-fossa | | 150,000 |
| SU_ATRT002 | 2 | Male | Primary resection | Supratentorial | | 150,000 |
| sPNET | 9 | Female | Primary resection | | | 80,000 |
| SU_MB002 | 3 | Male | Obtained at autopsy | Leptomeningeal spread | Group 3 | 30,000 |
| SU_MB009 | 9 | Female | Primary resection | | Group 4 | 80,000 |

TABLE 2-continued

General characteristics of cell lines used in the study

| Cell line | Age at diagnosis (years) | Gender | Primary resection/ Post therapy | Site of resection | Known mutations/ Subgroups | Number of injected cells in vivo |
|---|---|---|---|---|---|---|
| SU_MB012 | 6 | Male | Primary resection | Primary site | Group 3 | |
| SU_MB014 | | | | | Group 3 | |
| D283 | 6 | Male | Primary resection | Metastatic site: peritoneum | Group 3 | 30,000 |
| D425 | 5 | Male | | | Group 3 | 30,000 |
| D425s | 10 | Male | Primary resection of recurred tumor post therapy | | Group 3 | 30,000 |
| GL261 | Mouse glioma line | | | | | 300,000 |

Description of therapeutic antibody used (Hu5F9-G4). Hu5F9-G4 was constructed using CDR-grafting from a mouse anti-human CD47 antibody, clone 5F9. Because Hu5F9-G4 activity is primarily dependent on blocking the CD47-SIRPα interaction, a human IgG4 scaffold was selected to minimize the recruitment of Fc-dependent effector functions such as antibody-dependent cellular cytotoxicity, antibody-dependent cellular phagocytosis, and complement-dependent cytotoxicity. The mechanism of action does not require these functions, and their presence may increase toxicity against normal cells. Hu5F9-G4 was engineered using a human kappa and IgG4 isotype with a Ser228Pro substitution to reduce Fab arm exchange. Detailed biochemical characterization and non-human primate safety assessment was previously published.

Primary tissue dissociation and generation of primary cell lines. Pediatric brain tumor tissue samples were obtained under IRB protocol ID 18672 after informed patient consent at the Lucile Packard Children's Hospital (Stanford, Calif.) in accordance with institutional review board protocols. For minors, consent was obtained from a parent or guardian. Human subjects approval was given under IRB number: 350 (Panel: 3). Tumor pathology and diagnosis were confirmed by the on call institutional neuropathologist. Samples were enzymatically dissociated to single cells by collagenase IV (1 mg/ml) and DNase I (250 units/ml), and cells were plated in neural stem cell expansion medium (NSCEM) consisting of Neurobasal (-A) (Invitrogen), B27 (-A) (Invitrogen), human-bFGF (20 ng/ml) (Shenandoah Biotech), human-EGF (20 ng/ml) (Shenandoah Biotech), human recombinant LIF (Millipore) (as required), and heparin (10 ng/ml)(28). Pediatric glioblastoma cells were plated in pediatric glioma stem cell expansion medium (GSCEM) consisting of Neurobasal (-A) (Invitrogen), B27 (-A) (Invitrogen), human-bFGF (20 ng/ml) (Shenandoah Biotech), human-EGF (20 ng/ml) (Shenandoah Biotech), human PDGF-AA (20 ng/ml), PDGF-BB (20 ng/ml) (Shenandoah Biotech), and heparin sulfate (10 ng/ml) (Sigma). Cells were grown for 2 passages and infected with EF1-GFP-T2A-Luciferase (Systems Biosciences, BLIV503MN-1), then allowed to re-form spheres. Cells were then double sorted for GFP and further passaged in neural stem cell medium. Human fetal brain tissue from gestational weeks 16 to 22 was obtained from a non-profit source (Stem Express) and dissociated to single cells using TryPLE (Life Technologies), then cultured in NSCEM, as described above.

Primary human pediatric brain tumor cell lines. The primary cell lines were generated at Stanford University in our laboratory or kindly provided by various collaborators as detailed below. All tumor lines were authenticated using short tandem repeat (STR) fingerprinting at the following 15 loci: D3S1358, TH01, D21S11, D18S51, Penta E, D5S818, D13S317, D7S820, D16S539, CSF1PO, Penta D, vWA, D8S1179, TPOX, FGA, AMEL. All cultures were routinely tested for *mycoplasma* contamination.

Pediatric glioma lines. SU_DIPGVI, SU_DIPGXIII, and JHH DIPG1 were from rapid autopsy specimens of patients who died from diffuse intrinsic pontine glioma after receiving radiation and chemotherapy. SU_pGBM001 and SU_pGBM002 were derived from surgically resected tumor samples of pediatric patients diagnosed with glioblastoma.

Atypical teratoid rhabdoid tumor lines. CHB-ATRT1 was derived from a surgical specimen of a tumor from the posterior fossa. SU_ATRT002 was derived from a supratentorial surgical specimen.

MB lines. D283 and D425 were generously provided by Dr. Darrell Bigner (Duke University, Durham, N.C.). D425s was subcloned from the original D425 for increased growth characteristics and incidence of spinal metastasis. SU_MB002 cells were derived postmortem from the leptomeningeal compartment of a child with metastatic, treatment-refractory (chemotherapy only) MB. SU_MB009 cells were derived from the primary surgical resection of a tumor in a child whose tumor recurred after therapy, and they have been described earlier. SU_MB012 and SU_MB014 were derived from the primary surgical resection of a tumor in a child whose tumor recurred after therapy. MYC amplification in the SU_MB002 and D425s cells was confirmed with NanoString nCounter v2 Cancer CN Codeset.

Human neural progenitor lines: Origin and maintenance. Neural progenitor line (NSC1) was derived from subventricular zone tissue surgically excised during a functional hemispherectomy in a child with refractory seizures. NSC2 was derived from human fetal brain tissue from gestational weeks 16 to 22. Human neural progenitor cell lines were routinely tested for multi-potency and neurosphere self-renewal using standard protocols (see Monje and Fisher, J Pediatr Rehabil Med 4, 31-36 (2011)).

GL261 mouse glioma cell line. GL261 was a kind gift from Dr Michael Lim (Johns Hopkins University). The GL261 murine glioma model was established in 1970 by chemical induction with methylcholanthrene. Tumors generated were serially transplanted subcutaneously and intracranially in C57BL/6 mice. The list of primary cell lines used in this study is shown in table 2.

Cell line maintenance. Primary pGBM and DIPG lines were maintained in serum-free glioma stem cell medium consisting of Neurobasal (-A) (Invitrogen), B27 (-A) (Invitrogen), human-bFGF (20 ng/ml) (Shenandoah Biotech), human-EGF (20 ng/ml) (Shenandoah Biotech), human PDGF-AA (20 ng/ml), PDGF-BB (20 ng/ml) (Shenandoah Biotech), and heparin sulfate (10 ng/ml). All patient-derived MB primary cells were maintained in NSCEM. The subventricular zone-derived neural stem cells were similarly maintained in NSCEM. All patient-derived cell lines were authenticated using sequence-tagged site fingerprinting. Each line was evaluated for its ability to fully recapitulate the tumor of origin by orthotopic transplantation into NSG mice and analysis of the engrafted tumors by H&E staining.

Orthotopic transplantation of brain tumors and neural progenitor cells. Early passage spheres were transduced with either GFP or Td-tomato and luciferase-encoding lentivirus, expanded in (GSCEM), and double sorted for GFP or Td-tomato expression to obtain a >95% luciferase-expressing population. The selected population was expanded in (GSCEM) and orthotopically injected into the site of tumor resection. pHGG and ATRT cells were injected 2 mm posterior to bregma, 2 mm lateral to midline, and 3-4 mm deep in the brain. MB, PNET, and DIPG cells were injected at coordinates 2 mm posterior to lambda on midline and 2 mm deep into 4-6-week-old NOD-SCIDγ mice. Fetal brain-derived NPCs were injected in the lateral hemisphere of 1 to 3-day-old pups.

Flow cytometry analysis. Surgical brain tumor specimens were dissociated to single cells and stained with anti-CD47-PE. Hematopoietic and endothelial cells were gated out using a lineage mixture of Pacific blue conjugated anti-CD45 and anti-CD31. For analysis of MB initiating cells in xenografts, tumor-bearing mouse brains were dissociated to single cells. Anti-H2kb and anti-H2kd (Biolegend) antibodies were used to gate out mouse cells, and anti-CD15-FITC (BD Biosciences: Clone MMA) mAb was used to identify CD15+ human MB initiating cells. Flow cytometric analysis and cell sorting were performed on the BD FACS aria II (Becton Dickinson). Appropriate isotype and fluorescence, minus one control, were used to define the background gates.

Osmotic pump implantation. To achieve continuous intraventricular CNS administration of the anti-CD47 antibody, osmotic pumps (Alzet Co., Model 1004; flow rate 0.11 μL/h) were loaded with 1.9 μg/μL of antibody (equivalent to previously established 10 mg/kg dosing) or phosphate-buffered saline (PBS) (control). Pumps were coupled to brain infusion kits (Alzet Co., Model 8851) and primed overnight at 37° C., 5% CO2. Osmotic pumps were implanted subcutaneously on the dorsum, slightly caudal to the scapulae, through a 2.5 cm midline incision. Using a stereotaxic apparatus, brain cannulae were inserted intraventricularly per predefined coordinates (2 mm posterior to bregma, 0.5 mm right of midline, 1 mm deep) after removal of periosteal connective tissue, and secured with dental cement (Stoelting Co.). At the time of animals' death, cannula patency and drug delivery were verified by comparing pump weight before and after implantation.

In vivo sequential co-transplant xenograft cytotoxicity model. Human fetal-derived neural progenitor cells expressing Td-tomato and luciferase were injected into the lateral ventricle, 0.5 mm lateral to midline, of neonatal NSG mouse pups at 1 to 3 days of age. Mice were followed with BLI to ensure engraftment and sustained expression of luciferase. Human progenitor engrafted mice were then injected with unlabeled human MB cells (SU_MB002) at 1.5 months of age. SU_MB002 was previously confirmed to have 100% penetrance in multiple cohorts. 14 d after tumor cell transplantation, the mice were randomized based on BLI values and treated with either Hu5F9-G4 or PBS. Human neural cell viability and proliferation were measured through subsequent BLI.

Immunohistochemistry. Expression of CD47 protein on primary tumor samples was evaluated on 4-μm thick OCT embedded fresh frozen tissue sections. Sections were fixed with acetone, blocked with 5% goat serum, and incubated with anti-CD47 antibody (0.2 μg/ml, Abcam ab3283) followed by goat anti-mouse Alexa488 (Invitrogen) secondary antibody and counter-stained with 4',6-diamidino-2-phenylindole (DAPI). The sections were mounted, and the imaging was done on a fluorescent microscope (Leica). Orthotopic tumor-bearing mouse brains were fixed in formalin and embedded in paraffin, and 8 μm sections were cut to reveal either coronal or sagittal views of the brains. Tissue sections were processed for standard H&E staining or for mouse macrophage markers using the anti-F4/80 (Abcam) antibody. The images were taken with a Nikon E1000M microscope with a Spot Flex camera.

In vitro phagocytosis assay. In vitro phagocytosis assay was performed as described before with both human and mouse macrophages analyzed by either FACS or microscopy. To obtain human monocytes, PBMCs collected from venous blood of healthy volunteers were separated on a Ficoll density gradient (GE Healthcare). CD14+ monocytes were positively selected to >95% purity by MACS using anti-CD14 microbeads (Miltenyi), then plated at $1\times10^6$/ml in 150×25 mm tissue culture plates in RPMI 1640 with 10% FBS, penicillin/streptomycin, glutamine, and HEPES. To generate monocyte-derived macrophages, monocytes were treated for 7 d with human recombinant M-CSF (25 ng/mL). Mouse macrophages were obtained from mouse bone marrow after 7 d of bone marrow cell plating with mouse colony stimulating factor.

For phagocytosis assays carried out by fluorescence microscopy, macrophages were stained with PKH26 (Sigma-Aldrich), and dissociated tumor cells were labeled with 2.5 μM carboxyfluorescein succinimidyl ester (CSFE) according to the manufacturer's description. Cells were co-incubated at a 1:2 ratio (macrophages:tumor cells) along with indicated antibodies (10 μg/ml) or human IgG controls and incubated for 2 h at 37° C. Wells were repeatedly washed to remove non-phagocytosed cells and subsequently imaged with an inverted microscope (Leica DMI6000B). The phagocytic index was calculated as the number of macrophages that had phagocytosed tumor cells per 100 macrophages. For FACS-based phagocytosis assay, CFSE labeled tumor cells were incubated with indicated antibodies (10 μg/ml) for 30 min at 37° C. before co-incubation with macrophages. Adherent macrophages were collected using TrypLE Express (Life Technologies) and incubated in serum-free medium. $5\times10^4$ macrophages were added to $1\times10^5$ CFSE-labeled live tumor cells per well for 4 h and returned to the incubator. Analysis was carried out by flow cytometry. Human macrophages were identified using anti-human CD11b-Alexa647 and anti-human CD14-APC/Cy7 (BioLegend). Phagocytosis assays for each tumor type were performed in triplicates and repeated at least two times.

Sorting of macrophage populations during phagocytosis. Macrophages (count 500,000) were incubated with MB cells (2 million) labeled with Calcein-AM (Life Technologies) in the presence of Hu5F9-G4 for 2 h. The population that was positive for macrophages (identified using anti-CD14 and anti-CD11b antibodies) and MB cells (identified with Calcein) was sorted, cytospun onto slides, stained with modified Wright-Giemsa Stain (Sigma-Aldrich) according to the manufacturer's instructions, and imaged with light microscopy.

Collection of cerebrospinal fluid. CSF sampling was performed from the cisterna *magna*, located between the cerebellum and dorsal surface of the spinal cord. The mouse was shaved in the neck area, anesthetized with isoflurane, and placed in a stereotaxic frame. A midline sagittal incision was made inferior to the occiput. The pyramid muscles were separated using blunt forceps. To get proper access to dura mater of the cisterna *magna*, the mouse head was repositioned making a 135-degree angle with the body. Subsequently, the dura mater of cisterna *magna* was punctured using a glass capillary. Five to ten microliters of clean CSF sample was drained from the cisterna *magna*. Samples testing positive for blood serum albumin or hemoglobin were discarded from analysis.

Enzyme-linked immunosorbent assay (ELISA) for testing Hu5F9-G4 levels in blood and CSF. Ninety-six-well plates (Costar, 9018) were coated with huCD47/mFc at a concentration of 1 µg/ml in PBS and incubated at 4° C. overnight. After the plates were blocked for 1 h with 0.4% bovine serum albumin in PBS at room temperature, mouse serum and CSF samples were added in four sequential dilutions. The plates were incubated for 1 h at room temperature. Ten micrograms/ml biotin-labeled mouse 5F9 was added to the wells in the presence of various concentrations of unlabeled Hu5F9-G4, and the plates were incubated at room temperature for 1 h. After three successive washing steps, the plates were then incubated with HRP conjugated goat anti-human kappa-specific antibody for 1 h at room temperature. Plates were developed with OPT. The reaction was stopped with 2M $H_2SO_4$, and the results were recorded as optical density units at 490 nM. GraphPad Prism (GraphPad Inc.) was used to analyze the data.

Mice. NOD.Cg-Prkdcscid Il2rgtm1Wjl/SzJ (NSG) and C57/BL6 mice were housed in specific pathogen-free conditions at a barrier facility at the Lokey Stem Cell Building at Stanford School of Medicine (Stanford, Calif.). All animal handling, surveillance, and experimentation were performed in accordance with and approval from the Stanford University Administrative Panel on Laboratory Animal Care (Protocol #26548 and 26209).

Tumor tissue dissociation. Tumor samples were enzymatically dissociated by collagenase IV (1 mg/ml) in dissociation solution containing HBSS with calcium/magnesium (Cellgro), non-essential amino acids (Cellgro), sodium pyruvate (Cellgro), sodium bicarbonate (Cellgro), HEPES (25 mM) (Cellgro), 1× Glutamax-1 (Cellgro), 1× antibiotic antimycotic (Cellgro), DNase, and collagenase IV (Worthington) at 37° C. The suspension was washed 2 times with HBSS and filtered using 100 µm and 40 µm filters, respectively. The cells were resuspended in 0.9 M sucrose gradient solution in HBSS without Ca/Mg (Cellgro) to remove debris and dead cells. The cells were treated with ACK/RBC lysis buffer (Gibco), washed twice in PBS, and were then ready to use. For neurosphere formation, single tumor cells were plated in tumor-stem medium (TSM) consisting of Neurobasal (-A) (Invitrogen), B27 (-A) (Invitrogen), human-bFGF (20 ng/ml) (Shenandoah Biotech), human-EGF (20 ng/ml) (Shenandoah Biotech), human recombinant LIF (Millipore), and heparin (10 ng/ml). Early passage spheres were transduced with either GFP or Td-tomato luciferase encoding lentivirus and expanded in TSM. After secondary tumor sphere formation, the GFP or Td-tomato-positive cells were double sorted to obtain a pure population. The selected population was expanded in TSM medium and then injected intracranially into 5-6-week-old NSG mice using the stereotaxic frame.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of treating a metastatic pediatric brain tumor in an individual, the method comprising:
   administering by direct central nervous system delivery to the individual with a pediatric brain tumor anti-CD47 antibody hu5F9-G4 at a dose of from 10 mg/kg to 50 mg/kg effective to increase depletion of pediatric brain tumor cell and reduce metastasis to the meninges and/or spine.

2. The method of claim 1, wherein the metastatic pediatric brain tumor is a malignant glioma.

3. The method of claim 2, wherein the glioma is a high grade glioblastoma.

4. The method of claim 2, wherein the glioma is diffuse intrinsic pontine glioma.

5. The method of claim 1, wherein the pediatric brain tumor is an embryonal cancer selected from medulloblastoma, atypical teratoid rhabdoid tumor, and primitive neuroectodermal tumor.

6. The method of claim 1, wherein the metastatic pediatric brain tumor is a medulloblastoma.

7. The method of claim 1, wherein the metastatic pediatric brain tumor is an atypical teratoid rhabdoid tumor.

8. The method of claim 1, wherein the metastatic pediatric brain tumor is a primitive neuroectodermal tumor.

9. A method of treating a metastatic pediatric brain tumor in an individual, the method comprising:
   administering to the individual with a pediatric brain tumor by direct central nervous system delivery with an implantable continuous delivery device implanted in the ventricles of the brain, anti-CD47 antibody hu5F9-G4 at a dose of from 10 mg/kg to 50 mg/kg effective to increase depletion of pediatric brain tumor cells and reduce metastasis to the meninges and/or spine.

10. The method of claim 9, wherein anti-CD47 antibody hu5F9-G4 is also delivered systemically.

11. The method of claim 1, further comprising administration of a priming dose of the hu5F9-G4 antibody.

12. A method of treating metastasis to the meninges and/or spine for a pediatric medulloblastoma in an individual, the method comprising:

administering by intraventricular CNS administration to the individual with a metastatic pediatric medulloblastoma anti-CD47 antibody hu5F9-G4 at a dose of from 10 mg/kg to 50 mg/kg effective to increase depletion of medulloblastoma cells metastasized to the meninges and/or spine; and administering systemically anti-CD47 antibody hu5F9-G4 at a dose of from 10 mg/kg to 50 mg/kg effective to decrease volume of the primary tumor.

* * * * *